United States Patent
Chappelow et al.

(10) Patent No.: US 7,232,852 B2
(45) Date of Patent: Jun. 19, 2007

(54) PHOTOPOLYMERIZABLE COMPOSITIONS THAT INCLUDE ALICYCLIC/AROMATIC DIOXIRANES AND NOVEL DIOXIRANYL TETRAOXASPIRO [5.5] UNDECANES

(75) Inventors: Cecil C. Chappelow, Leawood, KS (US); Charles S. Pinzino, Kansas City, MO (US); J. David Eick, Gladstone, MO (US); Andrew J. Holder, Shawnee, KS (US); Shin-Shi Chen, Kansas City, MO (US); Li Jeang, Kansas City, MO (US)

(73) Assignee: Curators of the University of Missouri, Columbia, MO (US)

( * ) Notice: Subject to any disclaimer, the term of this patent is extended or adjusted under 35 U.S.C. 154(b) by 319 days.

(21) Appl. No.: 10/784,082

(22) Filed: Feb. 20, 2004

(65) Prior Publication Data

US 2004/0167245 A1 Aug. 26, 2004

Related U.S. Application Data

(62) Division of application No. 10/091,791, filed on Mar. 5, 2002, now Pat. No. 6,825,364.

(51) Int. Cl.
*A61K 6/00* (2006.01)
*A61K 6/08* (2006.01)
*C07D 319/00* (2006.01)
*C08F 4/26* (2006.01)

(52) U.S. Cl. ............... 522/169; 522/168; 522/170; 522/25; 522/908; 522/31; 523/105; 523/115; 523/116; 523/114; 523/118; 549/335

(58) Field of Classification Search ............... 522/103, 522/100, 113, 122, 134, 143, 167, 168, 170, 522/169, 183, 181, 908; 523/105, 114, 115, 523/116, 118; 549/335
See application file for complete search history.

(56) References Cited

U.S. PATENT DOCUMENTS

| | | | |
|---|---|---|---|
| 5,556,896 A | 9/1996 | Byerley et al. | |
| 5,808,108 A | 9/1998 | Chappelow et al. | |
| 6,022,940 A | 2/2000 | Byerley et al. | |
| 6,458,865 B2 * | 10/2002 | Chappelow et al. | 522/14 |
| 6,653,486 B2 * | 11/2003 | Chappelow et al. | 549/335 |
| 2002/0013380 A1 * | 1/2002 | Chappelow et al. | 522/14 |
| 2003/0119931 A1 * | 6/2003 | Oxman et al. | 522/14 |

OTHER PUBLICATIONS

Moszner et al, New Developments of polymeric dental composites. Progress in Polymer Science 26 (2001) pp. 535-576.*
Harris, C. D., A. J. Holder, J. D. Eick, and C. C. Chappelow, "AM1 Semiempirical Computational Analysis of the Homopolymerization of Spiroorthocarbonate," *Journal of Molecular Structure* (Theochem), 507, 265-275 (2000).
Kostoryz, E. L., P. Y. Tong, C. C. Chappelow, J. D. Eick, A. G. Glaros, and D. M. Yourtee, "In Vitro Toxicity of Spiroorthocarbonate Monomers Designed for Non-Shrinking Restorative," *Journal of Biomaterials Science*, Polymer Edition, 11(2), 187-196 (2000).
Chappelow, C. C., C. S. Pinzino, L. Jeang, C. D. Harris, A. J. Holder, and J. D. Eick, "Photoreactivity of Expanding Monomers and Epoxy-Based Matrix Resin Systems," *Journal of Applied Polymer Science*, 76, 1715-1724, (2000).
Eick, J. D., G. M. Kaufman, C. S. Pinzino, B. Morrison, and C. C. Chappelow, "New Prototype Epoxy-Based Low-Shrinkage/Low-Stress Composites," *Journal of Dental Research*, 79(SI), 148 (2000).
Chappelow, C. C., C. S. Pinzino, G. M. Kaufman, L. Jeang, A. J. Holder, and J. D. Eick, "Photoreactivity of Epoxy-Based Matrix Resins and Composites Containing Expanding Monomers," *Journal of Dental Research*, 79(SI), 148 (2000).
Kostoryz, E. L., P. Y. Tong, C. C. Chappelow, A. G. Glaros, J. D. Eick, and D. M. Yourtee, "Good Biocompatibility Profile of Novel Spiroorthocarbonate Expanding Monomers," *Journal of Dental Research*, 79(SI), 316 (2000).
Holder, A. J., D. A. White, C. D. Harris, C. C. Chappelow, and J. D. Eick, "Computational Energetic and Mechanistic Study of Various Expanding Monomers," *Journal of Dental Research*, 78(SI), 288 (1999).
Chappelow, C. C., C. S. Pinzino, J. D. Oxman, S. S. Chen, and J. D. Eick, "Photopolymerizable Expanding Matrix Resin Systems for Low Stress Composites," *Journal of Dental Research*, 78(SI), 371 (1999).
Pinzino, C. S., C. C. Chappelow, J. D. Oxman, J. A., Morrill, M. D. Power, and J. D. Eick, "Experimental Photocurable Adhesive Formulations Containing Expanding Monomers and Reaction Promoters," *Journal of Dental Research*, 78(SI), 315 (1999).

(Continued)

Primary Examiner—Sanza L. McClendon
(74) Attorney, Agent, or Firm—Stinson Morrison Hecker LLP

(57) ABSTRACT

A visible light cationically photopolymerizable composition is provided. This composition includes an expanding monomer and a dioxirane. More specifically, the expanding monomer used in this composition is one or more dioxiranyl tetraoxaspiro[5.5]undecanes. The composition of the present invention may be used as a matrix resin for dental restorative materials. Another embodiment of the present invention is various novel dioxiranyl tetraoxaspiro[5.5]undecanes.

17 Claims, 27 Drawing Sheets

OTHER PUBLICATIONS

Harris, C. D., A. J. Holder, C. C. Chappelow, and J. D. Eick, "Homopolymerization of Spiroorthocarbonate: A Computational Study," *Journal of Dental Research*, 77(SI), 154 (1998).

White, D. A., A. J. Holder, C. D. Harris, C. C. Chappelow, and J. D. Eick, "Computational Energetic and Mechanistic Study of Epoxide and Spiroorthocarbonate Polymerization," *Journal of Dental Research*, 77(SI), 154 (1998).

Chappelow, C. C., C. S. Pinzino, L. Jeang, C. D. Harris, a. J. Holder, and J. D. Eick, "Photoreactivity of Expanding Monomers in Dental Matrix Resins," *Journal of Dental Research*, 77(SI-B), 639 (1998).

Chappelow, C. C., C. S. Pinzino, C. D. Harris, A. J. Holder, and J. D. Eick, "Photoreactivity of Substituted 1,5,7,11-Tetraoxaspiro[5.5]undecane/Diepoxide/Polyol Matrix Resin Systems," *Journal of Dental Research*, 77(SI), 154 (1998).

Chappelow, C. C., C. S. Pinzino, M. D. Power, and J. D. Eick, "Photocured Epoxy/SOC Matrix Resin Systems for Dental Composites," *Polymer Preprints*, 38(2), 90 (1997).

Kostoryz, E. L., P. Y. Tong, R. R. Williams, J. D. Eick, C. C. Chappelow, and D. M. Yourtee, "Reduced Cytotoxicity of New Dental Resins Containing Spiroorthocarbonate/Epoxy Copolymers," *Journal of Dental Research*, 76(SI), 321 (1997).

Pinzino, C. S., C. C. Chappelow, M. D. Power, and J. D. Eick, "Visible Light Induced Polymerization Studies of SOCs and Monofunctional Epoxides," *Journal of Dental Research*, 76(SI), 41 (1997).

Chappelow, C. C., C. S. Pinzino, M. D. Power and J. D. Eick, "Photopolymerization of Epoxy/Polyol Mixtures Containing Spiroorthocarbonates," *Journal of Dental Research*, 76(SI), 40 (1997).

Rose, L. A., P. Y. Tong, J. D. Eick, C. C. Chappelow, and D. M. Yourtee, "A Study of the Mutagenicity of Non-shrinking Spiroorthocarbonate Co-polymers," *Journal of Dental Research*, 75(SI), 329 (1996).

Murphy, J., R. P. Chappell, J. D. Eick, and C. C. Chappelow, "Effect of Spiroorthocarbonate Addition on Polymerization Shrinkage of Acrylate Systems," *Journal of Dental Research*, 74(SI), 182 (1995).

Chappelow, C. C., C. S. Pinzino, J. M. DeHaan, F. Millich, and J. D. Eick, "Synthesis and Photopolymerization of Substituted 1, 5, 7, 11-Tetraoxaspiro[5.5]undecanes," *Journal of Dental Research*, 74(SI), 492 (1995).

Eick, J. D., T. J. Byerley, R. P. Chappell, G. P. Chen, C. Q. Bowles, and C. C. Chappelow, "Properties of Expanding SOC/Epoxy Copolymers for Dental Use," *Dental Materials*, 9, 123-127 (1993).

Byerley, T. J., J. D. Eick, G. P. Chen, C. C. Chappelow, and F. Millich, "Synthesis and Polymerization of New Expanding Dental Monomers," *Dental Materials*, 8, 345-350 (1992).

Chappelow, C. C., C. S. Pinzino, L. Jeang, C. D. Harris, A. J. Holder, and J. D. Eick, "Photoreactivity of Expanding Monomers and Epoxy-Based Matrix Resin Systems," *Journal of Applied Polymer Science*, 76, 1715-1724 (2000).

Mues, Peter et al., "A New Approach to Spiroorthocarbonates . . . ", CA 113:97535, 1990.

Endo, Takeshi et al., "Adhesives for Catherer Tubes . . . ", CA 129: 19721, 1998.

Thompson et al., "Dental Resins with Reduced Shrinkage During Hardening," *Journal of Dental Research*, vol. 58, pp. 1522-1532, 1979.

Stansbury, "Improved Monomers for Double Ring-Opening Polymerization with Expansion," *Journal of Dental Research*, vol. 70, p. 527, Abstract No. 2088, 1991.

Byerley et al., "Expandable Matrix Monomers for Dental Composites," *Journal of Dental Research*, vol. 69, p. 263, Abstract No. 1233, 1990.

Sadhir et al., "Expanding Monomers: Synthesis, Characterization and Applications," CRC Press, Boca Raton, p. 329-332, 1992.

* cited by examiner

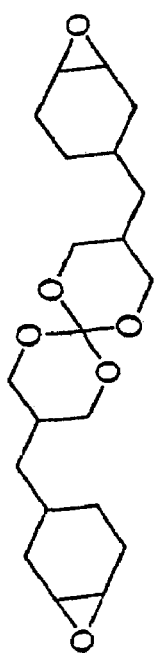
FIG. 36.

PHOTOPOLYMERIZABLE COMPOSITIONS THAT INCLUDE ALICYCLIC/AROMATIC DIOXIRANES AND NOVEL DIOXIRANYL TETRAOXASPIRO [5.5] UNDECANES

CROSS-REFERENCE TO RELATED APPLICATIONS

This application is a divisional of and claims priority from application Ser. No. 10/091,791, entitled "Novel Dioxiranyl Tetraoxaspiro[5.5]Undecanes" filed Mar. 5, 2002, now U.S. Pat. No. 6,825,364 and is incorporated by reference in its entirety.

STATEMENT REGARDING FEDERALLY SPONSORED RESEARCH OR DEVELOPMENT

Not Applicable.

FIELD OF THE INVENTION

This invention relates in general to compositions of matter and, more particularly, to compositions that include an expanding monomer, which may be one of the novel dioxiranyl tetraoxaspiro[5.5]undecanes (TOSU) disclosed herein, and a dioxirane. These compositions may also include a polyol, a photoinitiator, a photosensitizer and/or a reaction promoter. The polymerizable compositions of the present invention are useful for a variety of applications, including use as dental materials, such as composites.

BACKGROUND OF THE INVENTION

Many types of monomers undergo shrinkage during polymerization to a degree that makes them generally unsuited for use in numerous applications, including for use as stress-free composites, high-strength adhesives, and precision castings. As an example, when such monomers are used in composites which contain inorganic fillers, the polymeric matrix is subject to failure when the polymer shrinks and pulls away from the filler particles. Failure of the composite can also occur when the matrix ruptures as a result of voids or micro cracks which form in the matrix during polymerization shrinkage.

Polymeric matrices commonly employed in dental materials such as adhesives and composites are based on 2,2'-bis[4-(2-hydroxy-3-methacryloyloxypropoxy)]phenyl propane (BisGMA). A significant problem associated with the use of this monomer in dental applications is the shrinkage which occurs as the monomer is polymerized. The BisGMA monomer itself typically experiences high shrinkage, and when a low viscosity reactive diluent is combined with the monomer, the shrinkage may even be higher. The adverse effects of such shrinkage are believed to include increased postoperative sensitivity, the formation of marginal gaps between the dental restoration and the cavity wall, cracking of the restoration, and microleakage and potential failure of the restoration.

The discovery that spiroorthocarbonates may undergo reduced polymerization contraction and possibly polymerization expansion has led to the suggestion of their use in reinforced composites, including as dental materials. Spiroorthocarbonates are esters of orthocarboxylic acid and have four oxygen atoms bonded to a single carbon atom, with the carbon atom being common to two ring systems. The expansion of the spiroorthocarbonates on polymerization is attributed to a double spiro-cyclic ring opening of the spiroorthocarbonates, resulting in the breaking of two covalent bonds to form one new bond.

Initial attempts to form a homogeneous polymer matrix from certain spiroorthocarbonates and BisGMA resin mixtures proved unsuccessful because of the incomplete polymerization of the spiroorthocarbonates. Thompson et al., J. Dental Research 58:15221532 (1979). More recent studies demonstrated that homogeneous mixtures of other spiroorthocarbonates and BisGMA could be obtained. Stansbury, J. Dental Research 70:527; Abstract No. 2088 (1991).

The photocationic-initiated expansion polymerization of alicyclic spiroorthocarbonate monomers and the potential use of the resulting polymers in dental materials have been previously reported by some of the present inventors, with others. Byerley et al., Dent. Mater. 8:345-350 (1992). The specific spiroorthocarbonates identified by Byerley et al. include cis/cis, cis/trans, and trans/trans configurational isomers of 2,3,8,9-di(tetramethylene)-1,5,7,11-tetraoxaspiro [5.5]undecane. These spiroorthocarbonates were determined to undergo an expansion of 3.5% during homopolymerization and demonstrated acceptable cytotoxicity and genotoxicity properties, making them promising components of composite resin matrix materials.

Some of the present inventors, with others, have also previously reported on the preparation of a copolymer of an alicyclic spiroorthocarbonate and an unidentified monofunctional epoxide, with the observation that there were no indications of the formation of small ring compounds as polymerization by-products. Byerley et al., J. Dental Research 69:263; Abstract No. 1233 (1990). The copolymerization of trans/trans-2,3,8,9-di(tetramethylene)-1,5,7, 11-tetraoxaspiro[5.5]undecane and commercially available multifunctional epoxides was also disclosed in a paper presented by Byerley et al., Abstract No. 1233, cited above. However, no physical or mechanical properties, including percentage shrinkage, of the copolymer compositions were disclosed. Still further, spiroorthocarbonate copolymers have been created that are capable of yielding a hard, non-shrinking matrix resin. These copolymers include a trans/trans-2,3,8,9-di(tetramethylene)-1,5,7,11-tetraoxaspiro[5.5]undecane spiroorthocarbonate, a polymerizable epoxy resin, and a hydroxyl containing material, as described in U.S. Pat. No. 5,808,108.

A diepoxy spiroorthocarbonate, namely, 3,23-dioxatrispiro[tricyclo[3.2.1.0<2,4>]octane-6,5'-1,3-dioxane-2'2"-1,3-dioxane-5",7"'-tricyclo[3.2.1.0<2,4>octane], is disclosed in a book entitled, "Expanding Monomers, Synthesis, Characterization and Applications," edited by R. J. Sadhir and R. M. Luck, CRC Press, Boca Raton (1992), pp. 329-332.

Some of the present inventors, with others, have previously disclosed the spiro-orthcarbonates 2,8-dimethyl-1,5, 7,11-tetraoxaspiro[5,5]undecane and 3,9-diethyl-3,9-dipropionyloxymethyl-1,5,7,11-tetraoxaspiro[5,5]undecane in an article entitled "Photoreactivity of Expanding Monomers and Epoxy-Based Matrix Resin Systems" by Chappelow et al., J. of Applied Polymer Science, Vol 76, 1715-1724 (2000).

However, none of the above disclosed spiro-orthocarbonates used in a photopolymerizable composition generally exhibit characteristics desirable in a dental restorative, including flexible linkages, enhanced miscibility and reactivity and reduced photopolymerization contraction stress.

Despite the advances resulting from the above-noted polymeric compositions and SOCs, a need still exists for cationically photopolymerizable compositions exhibiting properties such as reduced shrinkage and reduced photopolymerization contraction stress. Still further, there is a need for expanding monomers containing flexible linkages that provide enhanced miscibility and reactivity in photopolymerizable compositions.

SUMMARY OF THE INVENTION

A visible light cationically photopolymerizable composition is provided. This composition includes an expanding monomer and a dioxirane. More specifically, the expanding monomer used in this composition is one or more dioxiranyl tetraoxaspiro[5.5]undecanes. The composition of the present invention may be used as a matrix resin for dental restorative materials. Still further, as another embodiment of the present invention, various novel dioxiranyl tetraoxaspiro[5.5]undecanes are provided.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

In the accompanying drawings, which form a part of the specification and are to be read in conjunction therewith:

FIG. 36 is the $^1$C-NMR spectrum of 3,9-bis(cyclohex-3-enylmethyl)-1,5,7,11-tetraoxaspiro[5,5]undecane;

DETAILED DESCRIPTION OF THE PREFERRED EMBODIMENTS

Figure 1:
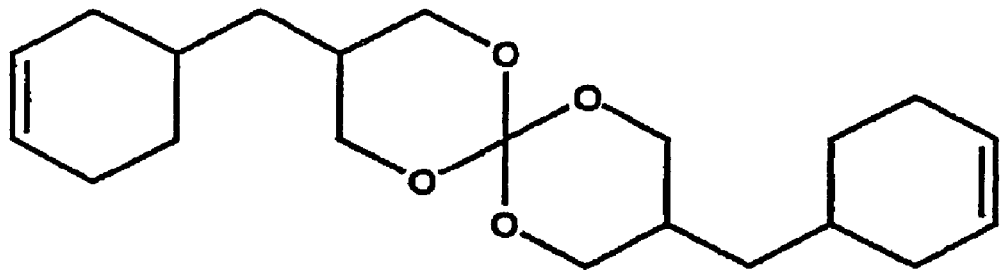
FIG. 1 is the structural formula of 3,9-bis(cyclohex-3-enylmethyl)-1,5,7,11-tetraoxaspiro[5,5]undecane.

The present invention relates to photopolymerizable oxirane/1,5,7,11tetraoxaspiro[5.5]undecane based compositions containing functional components. These compositions can be used as dental matrix resins. More specifically, the composition of the present invention includes a dioxirane (DO) and a dioxiranyl tetraoxaspiro[5.5]undecane, which can undergo polymerization with reduced shrinkage. The latter component may also be referred to as an expanding monomer. The specific type of expanding monomers utilized in the composition of the present invention may be classified as 1,5,7,11-tetraoxaspiro[5.5]undecane (TOSU) derivatives. By using a dioxiranyl TOSU, the composition has the potential of reducing the amount of polymerization shrinkage of the total formulation.

The formulation further may include a polyol (PL) and/or a reaction promoter (RP). The reaction promoter is capable of accelerating the photopolymerization rate of the formulation. When proportionally formulated, homogeneous reaction mixtures of the present invention are capable of rapidly undergoing photoinitiated polymerization with less volume shrinkage and yielding polymerization with less stress than the corresponding dioxirane/polyol mixtures that do not contain a dioxiranyl TOSU monomer. In addition, the dioxirane/dioxiranyl TOSU/polyol resins of the present invention have the potential of forming chemical bonds with substrates containing multifunctional groups.

Still further, the formulation of the present invention may include a photoinitiator (PI) and/or a photosensitizer (PS). The polyol, reaction promoter and photosensitizer are optional components, and none, one, some or all of these components may be present in the formulation. These optional components may be used to create dental matrices with particular desired properties. Preferably the composition is cationically polymerizable by visible light. Preferably, the compositions of the subject invention are matrix resins for dental restorative materials. The two main classes of photopolymerizable compositions within the scope of this invention are identified as DO/TOSU mixtures and DO/TOSU/PL mixtures.

Examples of novel TOSUs that may be used in the composition of the present invention include, but are not limited to, 3,9-sis(cyclohex-3-enylmethyl)-1,5,7,11-tetraoxaspiro[5.5]undecane (BCHEM), 3,9-bis[(7-oxabicyclo[4.1.0]hept-3-yl)methyl]-1,5,7,11-tetraoxaspiro[5.5]undecane (BOCHM), 3,9-bis[(6-methylcyclohex-3-enyl)methyl]-1,5,7,11tetraoxaspiro[5.5]undecane (BMCHEM), 3,9-bis[(4-methyl-7-oxabicyclo[4.1.0]hept-3-yl)methyl]-1,5,7,11-tetraoxaspiro[5.5]undecane (BMOCHM), 3,9-bis(cyclohex-3-enylmethoxy)-1,5,7,11-tetraoxaspiro[5.5]undecane (BCHEMO), 3,9-bis[(7-oxabicyclo[4.1.0]hept-3-yl)methoxy]-1,5,7,11-tetraoxaspiro[5.5]undecane (BOCHMO), 3,9-bis[2-methyl-7-oxabicyclo[4.1.0]hept-3-yl)methoxy]-1,5,7,11-tetraoxaspiro[5.5]undecane (BMCHEMO), 3,9-bis[(4-methyl-7-oxabicyclo[4.1.0]hept-3-yl)methoxy]-1,5,7,11-tetraoxaspiro[5.5]undecane (BMOCHMO), 3,9-bis(cyclohex-3-enyloxymethyl)-1,5,7,11-tetraoxaspiro{5.5}undecane (BCHEOM), 3,9-bis[7-oxabicyclo[4.1.0]hept-3-yl)oxymethyl]-1,5,7,11-tetraoxaspiro[5.5]undecane (BOCHOM), 3,9-bis[(6-methylcyclohex-3-enyl)oxymethyl -1,5,7,11-tetraoxaspiro[5.5]undecane (BMCHEOM), and 3,9-bis[(4-methyl-7-oxabiclo[4.1.0]hept-3-yl)oxymethyl]-1,5,7,11-tetraoxaspiro[5.5]undecane (BMOCHOM), 8,10,19,20-tetraoxatrispiro[5.2.2.5.2.2]henicosa-2,14-diene (TOTSHC), 7,26-dioxatrispiro[bicycle[4.1.0]heptane-3,5'-1,3-dioxane-2'2"-1,3-dioxane-5",4'''-bicyclo[4.1.0]heptane](DOTSHH), and combinations thereof. These novel TOSUs are shown in FIGS. 1-16.

Figure 17:
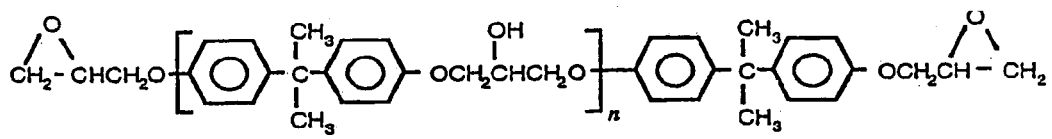
FIG. 17 is the structural formula of diglycidyl ether bisphenol A.
Figure 18:
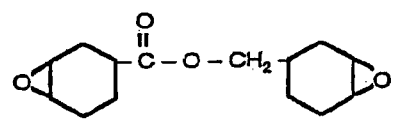
FIG. 18 is the structural formula of 3,4-epoxycyclohexanemethyl-3,4-epoxycyclohexane carboxylate.
Figure 19:
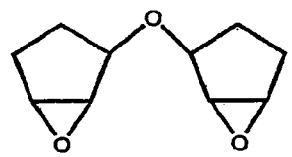
FIG. 19 is the structural formula of bis(2,3-oxiranylcyclopentyl) ether.
Figure 20:
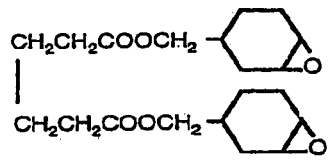
FIG. 20 is the structural formula of bis(3,4-epoxycyclohexylmethyleneoxy)adipate.
Figure 21:
FIG. 21 is the structural formula of butanediol diglycidyl ether.

The dioxirane may be alicyclic and/or aromatic. Examples of dioxiranes (DOs) include, but are not limited to, diglycidyl ether bisphenol A, which may be obtained from Ciba Geigy under the trade name GY6004 or Shell under the trade name EPON 825; 3',4'-epoxycyclohehanem-ethyl-3,4-epoxycyclohexane carboxylate, which may be obtained from Union Carbide under the tradename UVR 6105; bis(2,3-oxiranylcyclopentyl)ether (BOCPE), which may be obtained from Aldrich as number 45,567-9; butanediol diglycidyl ether, which may be obtained from Ciba-Geigy under the tradename RD 2; and bis(3,4-epoxycyclohexylmethyl) adipate, which may be obtained from Union Carbide under the tradename ERL-4299. Diglycidyl ether bisphenol A is shown in FIG. 17, 3',4'-epoxycyclohehanem-ethyl-3,4-epoxycyclohexane carboxylate is shown in FIG. 18, bis(2,3-oxiranylcyclopentyl)ether (BOCPE) is shown in FIG. 19, butanediol diglycidyl ether is shown in FIG. 20, and bis(3,4-epoxycyclohexylmethyl) adipate is shown in FIG. 21.

Figure 2:
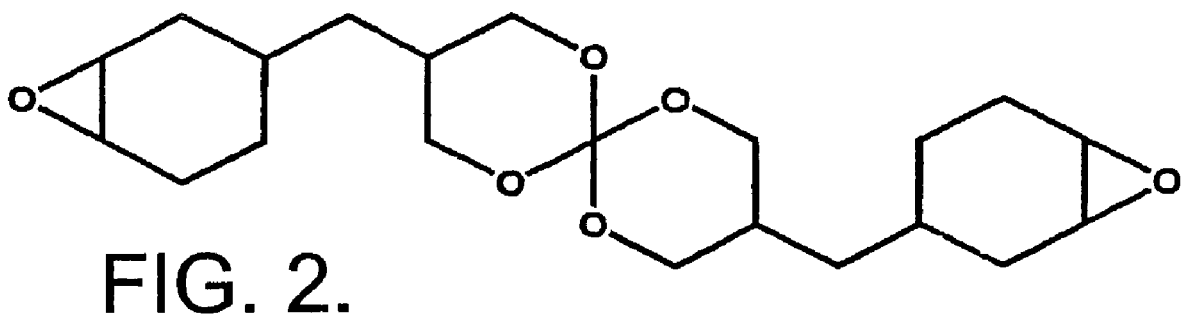
FIG. 2 is the structural formula of 3,9-bis[(7-oxabicyclo[4.1.0]hept-3-yl)methyl]-1,5,7,11-tetraoxaspiro[5.5]undecane.
Figure 3:
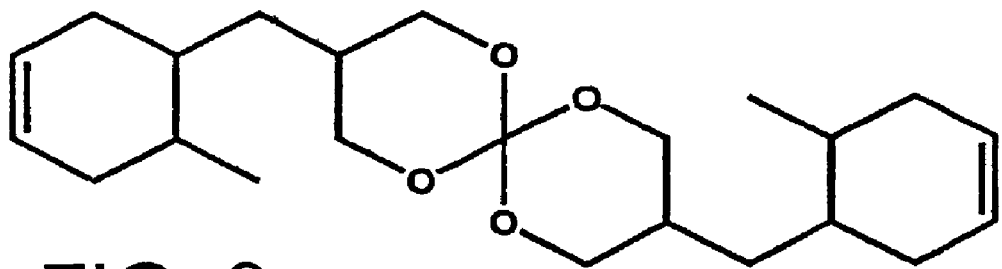
FIG. 3 is the structural formula of 3,9-bis[(6-methylcyclohex-3-enyl)methyl]-1,5,7,11-tetraoxaspiro[5,5]undecane.
Figure 22:
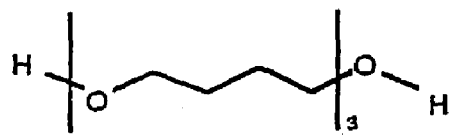
FIG. 22 is the structural formula of polytetrahydrofuran.
Figure 23:
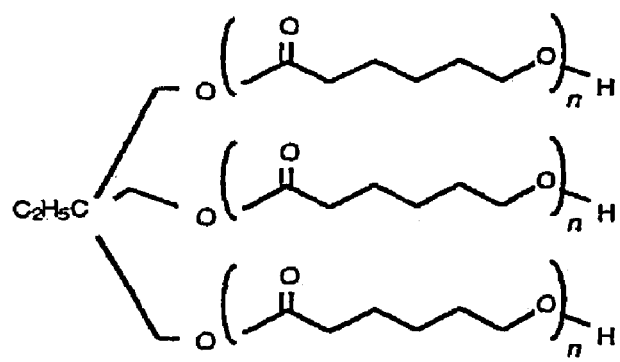
FIG. 23 is the structural formula of 2-oxepanone, polymer with 2-ethyl-2-(hydroxymethyl)-1,3-propane diol.

Examples of polyols (PLs) that may be used in the composition of the present invention include, but are not limited to, poly(tetrahydrofuran) (PTHF), average M=ca. 250, which may be obtained from Aldrich as number 34,526-1; 2-oxepanone polymer with 2-ethyl-2-(hydroxymethyl)-1,3-propane diol which may be obtained from Union Carbide under the tradename Tone 301; and combinations thereof. poly(tetrahydrofuran) (PTHF) is shown in FIG. 22, and 2-oxepanone polymer with 2-ethyl-2-(hydroxymethyl)-1,3-propane diol is shown in FIG. 23.

Figure 24:
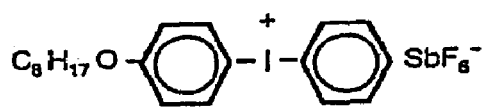
FIG. 24 is the structural formula of (4-n-octyloxyphenyl) phenyliodonium hexafluoroantimonate.
Figure 25:
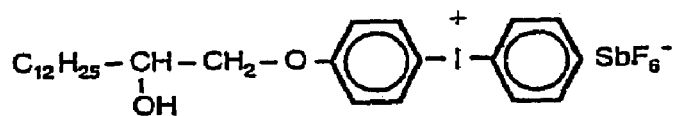
FIG. 25 is the structural formula of [4-(2-hydroxytetradecyloxyphenyl)]phenyliodonium hexfluoroantimonate.
Figure 26:
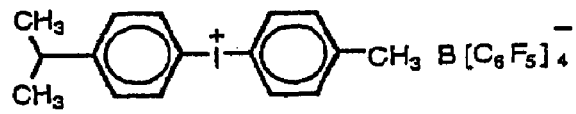
FIG. 26 is the structural formula of [4-(1-methylethyl)phenyl](4-methylphenyl)iodonium tetrakis(pentafluorophenyl)borate(1-)

A diaryliodonium salt may be the photoinitiator. Examples of other photoinitiators (PIs) that may be used in the composition of the present invention include, but are not limited to, (4-n-octyloxyphenyl)phenyliodonium hexafluoroantimonate (OPIA), which may be obtained from GE Silicones under number 479-2092C; [4-(2-hydroxytetradecyloxyphenyl)]phenyliodonium hexafluoroantimonate (CD 1012), which may be obtained from Sartomer under the tradename SarCat CD-1012 or from Gelest under the tradename OMAN072; [4-1-methylethyl)phenyl](4-methylphenyl)iodonium tetrakis(pentafluorophenyl)borate(1-) (RHO2074), which may be obtained from Rhodia, Inc., under the tradename Rhodorsil Photoinitiator 2074; and combinations thereof. (4-n-octyloxyphenyl)phenyliodonium hexafluoroantimonate (OPIA) is shown in FIG. 24, [4-(2-hydroxytetradecyloxyphenyl)]phenyliodonium hexafluoroantimonate (CD 1012) is shown in FIG. 25, and [4-1-methylethyl)phenyl](4-methylphenyl)iodonium tetrakis (pentafluorophenyl)borate(1-) (RHO2074) is shown in FIG. 26.

Figure 27:
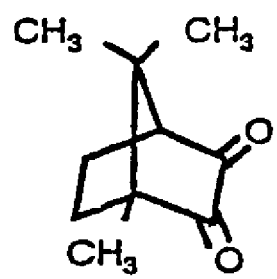
FIG. 27 is the structural formula of camphorquinone.
Figure 28:
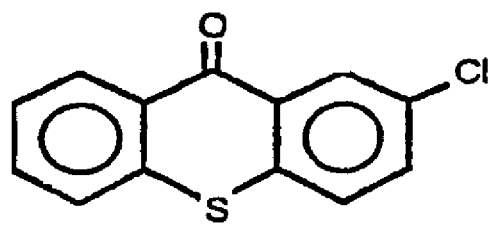
FIG. 28 is the structural formula of 2-chlorothioxanthen-9-one.

An alpha-dicarbonyl compound may be used as a photosensitizer. Examples of specific photosensitizers (PSs) that may be used in the composition of the present invention include, but are not limited to, (+/−) camphorquinone (CQ), which may be obtained from Aldrich under the number 12,489-2 with a 97% purity; 2-chlorothioxanthen-9-one (CTXO), which may be obtained from Aldrich C7 under the number 240-4; and combinations thereof. Camphorquinone (CQ) is shown in FIG. 27, and 2-chlorothioxanthen-9-one (CTXO) is shown in FIG. 28.

Figure 4:
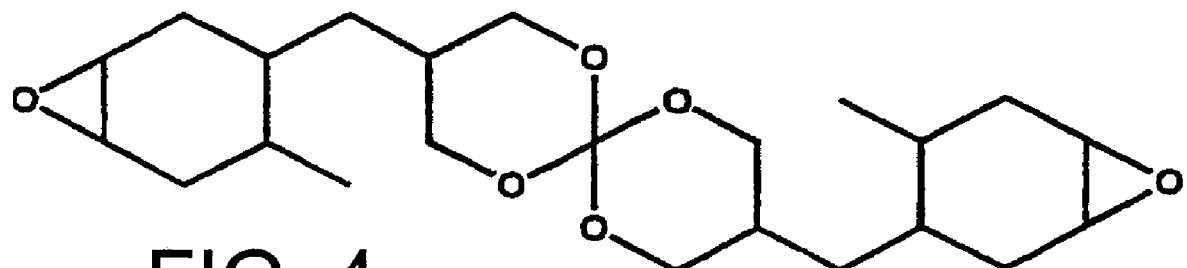
FIG. 4 is the structural formula of 3,9-bis[(4-methyl-7-oxabicyclo[4.1.0]hept-3-yl)methyl]-1,5,7,11-tetraoxaspiro[5,5]undecane.
Figure 5:
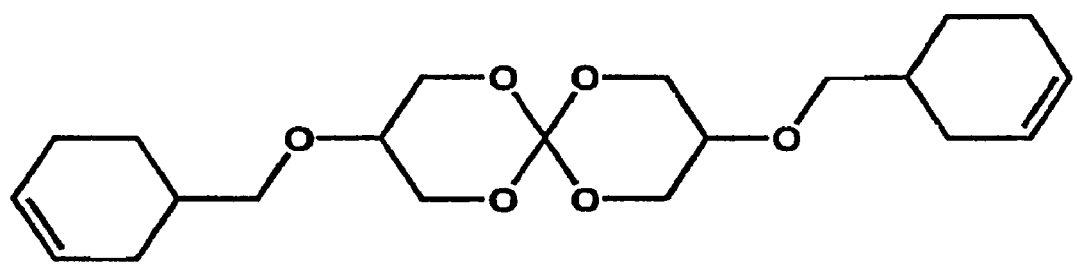
FIG. 5 is the structural formula of 3,9-bis(cyclohex-3-enylmethoxy)-1,5,7,11-tetraoxaspiro[5,5]undecane.
Figure 6:
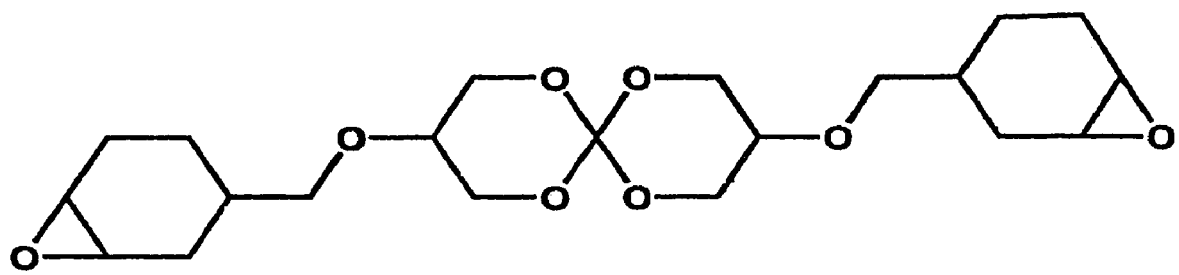
FIG. 6 is the structural formula of 3,9-bis[(7-oxabicyclo[4.1.0]hept-3-yl)methoxy]-1,5,7,11-tetraoxaspiro[5,5]undecane.
Figure 7:
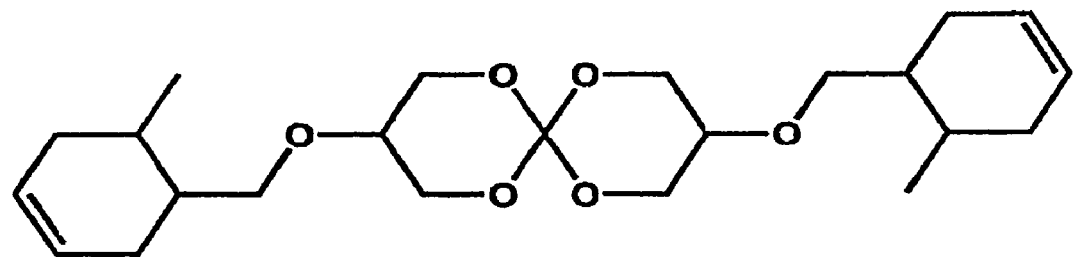
FIG. 7 is the structural formula of 3,9-bis[(6-methylcyclohex-3-enyl)methoxy]-1,5,7,11-tetraoxaspiro[5,5]undecane.
Figure 8:
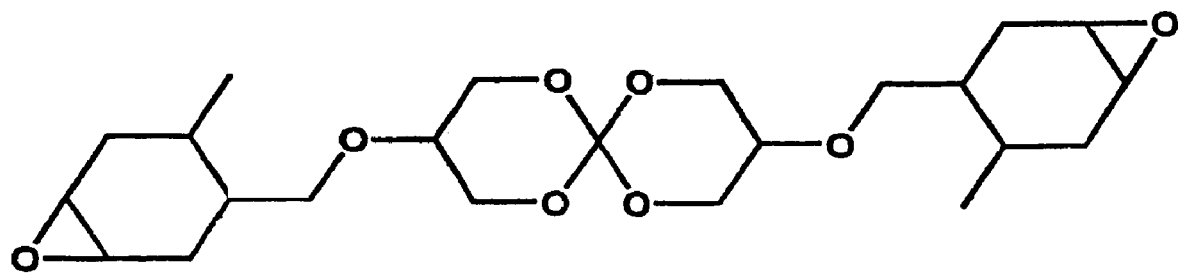
FIG. 8 is the structural formula of 3,9-bis[(4-methyl-7-oxabicyclo[4.1.0]hept-3-yl)methoxy]-1,5,7,11-tetraoxaspiro[5,5]undecane.
Figure 9:
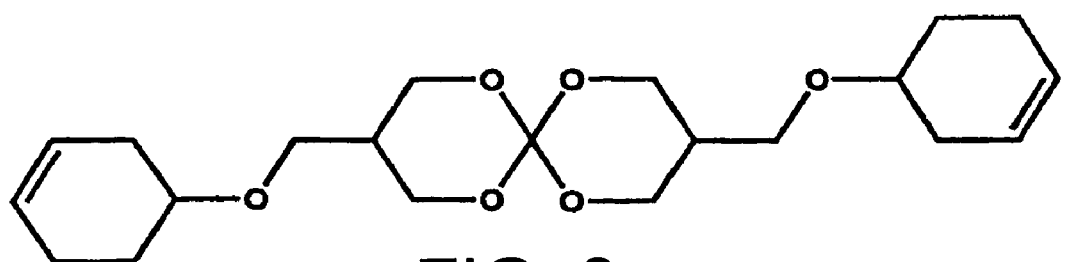
FIG. 9 is the structural formula of 3,9-bis(cyclohex-3-enyloxymethyl)-1,5,7,11-tetraoxaspiro[5,5]undecane.
Figure 10:
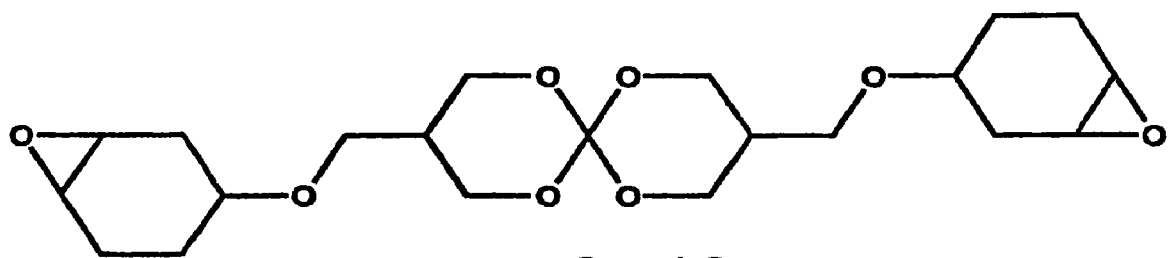
FIG. 10 is the structural formula of 3,9-bis[(7-oxabicyclo[4.1.0]hept-3-yl)oxymethyl]-1,5,7,11-tetraoxaspiro[5.5]undecane.
Figure 11:
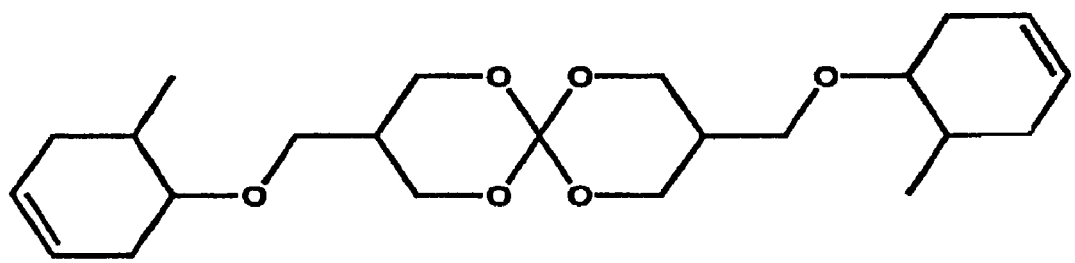
FIG. 11 is the structural formula of 3,9-bis[(6-methylcyclohex-3-enyl)oxymethyl]-1,5,7,11-tetraoxaspiro[5,5]undecane.
Figure 12:
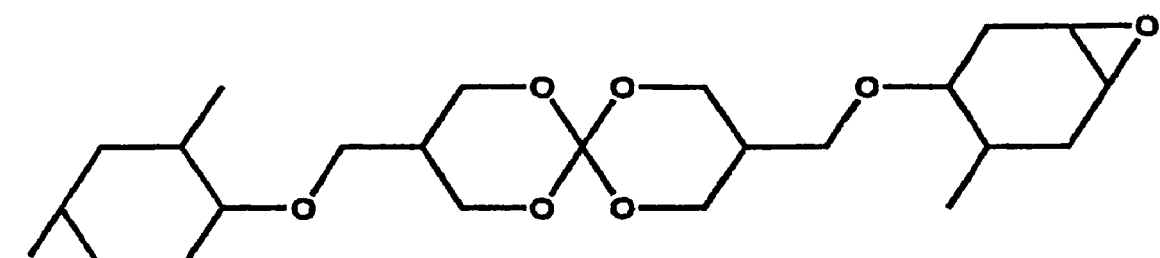
FIG. 12 is the structural formula of 3,9-bis[(4-methyl-7-oxabicyclo[4.1.0]hept-3-yl)oxymethyl]-1,5,7,11-tetraoxaspiro[5,5]undecane.
Figure 13:
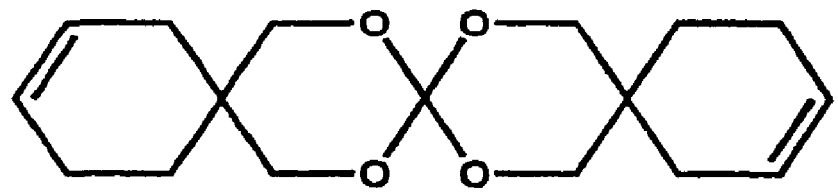
FIG. 13 is the structural formula of 8,10,19,20-tetraoxatrispiro[5.2.2.5.2.2]henicosa-2,14-diene.
Figure 14:
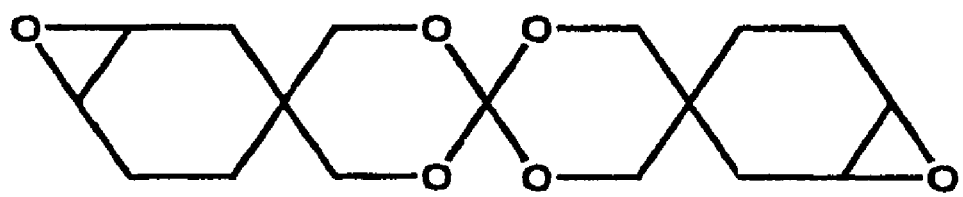
FIG. 14 is the structural formula of 7,26-dioxatrispiro[bicyclo[4.1.0]heptane-3,5'-1,3-dioxane-2',2''-1,3-dioxane-5'',4'''-bicyclo[4.1.0]heptane]
Figure 15:
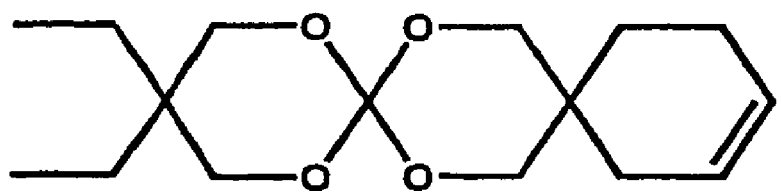
FIG. 15 is the structural formula of 3,3-diethyl-1,5,7,16-tetraoxadispiro[5.2.5.2]hexadec-11-ene.
Figure 16:
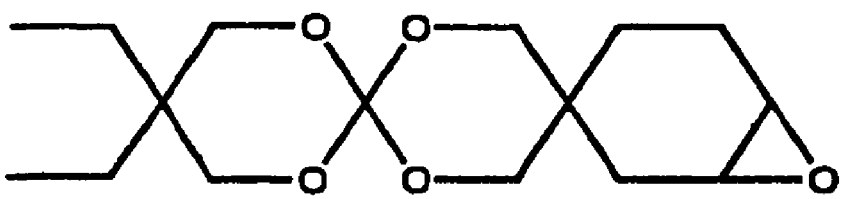
FIG. 16 is the structural formula of 5,5-diethyl-19-oxdispiro[1,3-dioxane-2,5'-1,3-dioxane-2',3''-bicyclo[4.1.0]heptane]
Figure 29:
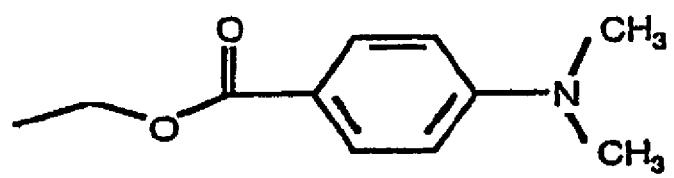
FIG. 29 is the structural formula of ethyl 4-dimethylaminobenzoate.
Figure 30:
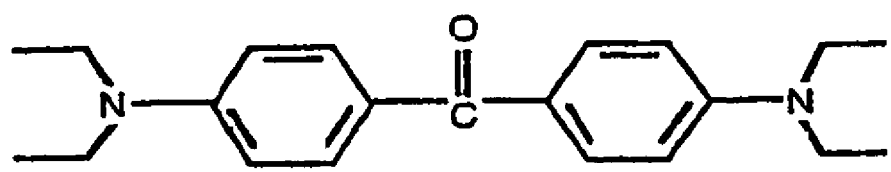
FIG. 30 is the structural formula of 4,4'-bis(diethylamino) benzophenone.

Examples of reaction promoters (RPs) that may be used in the composition of the present invention include, but are not limited to, ethyl p-dimethylaminobenzoate (EDMAB), which may be obtained from Acros under number 11840-1000 at 99+% purity; 4,4'-bis(diethylamino)benzophenone (BDEAB), which also may be obtained from Acros under number 17081-0250s at 99+% purity; and combinations thereof. Ethyl p-dimethylaminobenzoate (EDMAB) is shown in FIG. 29, and 4,4'-bis(diethylamino)benzophenone (BDEAB) is shown in FIG. 30.

The composition of the present invention is made by combining the above-described components together. The composition may then be cationically polymerized to form a dental matrix resin.

The dioxiranyl tetraoxaspiro[5.5]undecanes used in making the composition of the present invention are made by a series of reactions. First, an alkyl substituted unsaturated cyclohexenyl group bonded to a propane diol by a flexible alkylene, oxyalkylene, or an alkyleneoxy linkage is subjected to transesterification with tetra-alkyl-orthocarbonate to obtain an unsaturated 1,5,7,11-tetraoxaspiro[5.5]undecane (TOSU). Preferably, the flexible linkage is methylene, oxymethylene, or methyleneoxy. Preferable the tetra-alkyl orthocarbonate is tetra-ethyl orthocarbonate. This TOSU is then epoxidized with an organic per-acid to obtain a 1,5,7,11-dioxiranyl tetraoxaspiro[5.5]undecanes (TOSU). Preferably, the per-acid is metachloro-per-benzoic acid (MCPBA). The TOSUs listed above are novel compounds made by the method outlined above.

Examples 1-7, which follow, illustrate photopolymerizable mixtures of the present invention that have been formulated, polymerized, and characterized. Examples 8-10, which follow, show methods of making various novel TOSUs. These examples are not meant to limit the scope of this invention in any way.

EXAMPLE 1

Selected TOSU/BOCPE formulations representing 16 combinations of four different TOSUs (DOTSHH, DEODSH, BOCHM, BMOCHM) at four concentration levels (0.5, 1, 5, 10 wt %); one PI (OPIA); one PS (CQ); and one RP (EDMAB) were subjected to PDSC analysis. The amounts of components in the various formulations are shown in Table 1.

TABLE 1

TOSU/BOCPE Photopolymerizable Compositions

| No. | Dioxirane | TOSU | Wt. % |
|---|---|---|---|
| 1 | BOCPE | None | 0 |
| 2 | BOCPE | DOTSHH | 0.5 |
| 3 | BOCPE | DOTSHH | 1 |
| 4 | BOCPE | DOTSHH | 5 |
| 5 | BOCPE | DOTSHH | 10 |
| 6 | BOCPE | DEODSH | 0.5 |
| 7 | BOCPE | DEODSH | 1 |
| 8 | BOCPE | DEODSH | 5 |
| 9 | BOCPE | DEODSH | 10 |
| 10 | BOCPE | BOCHM | 0.5 |
| 11 | BOCPE | BOCHM | 1 |
| 12 | BOCPE | BOCHM | 5 |
| 13 | BOCPE | BOCHM | 10 |
| 14 | BOCPE | BMOCHM | 0.5 |
| 15 | BOCPE | BMOCHM | 1 |
| 16 | BOCPE | BMOCHM | 5 |
| 17 | BOCPE | BMOCHM | 10 |

Note:
Photoinitiator system: OPIA/CQ/EDMAB = 1/0.5/0.1 wt %

A comparison of the compositional and PDSC data is shown in Table 2. This data suggests that increasing the concentration of TOSU in the polymerizate mixture increases the polymerization rate as indicated by shorter exotherm peak maximum times.

TABLE 2

TOSU/BOCPE Photopolymerization Characteristics at 37° C.

| No. | ΔH (J/g) | Ind. time (sec) | Peak max. (sec) | k (min$^{-1}$) | Peak max. time improvement (%) |
|---|---|---|---|---|---|
| 1 | 282 | 32 | 84 | 1.5 | Reference |
| 2 | 311 | 27 | 79 | 4.0 | 6 |
| 3 | 284 | 35 | 77 | 5.5 | 8 |
| 4 | 321 | 21 | 57 | 2.1 | 32 |
| 5 | 289 | 22 | 46 | 6.4 | 45 |
| 6 | 318 | 34 | 96 | 3.1 | 0 |
| 7 | 266 | 32 | 76 | 2.5 | 0 |
| 8 | 319 | 24 | 70 | 3.2 | 0 |
| 9 | 312 | 23 | 67 | 2.8 | 0 |
| 10 | 296 | 29 | 77 | 4.4 | 11 |
| 11 | 330 | 22 | 64 | 2.4 | 24 |
| 12 | 311 | 18 | 43 | 1.2 | 49 |
| 13 | 295 | 17 | 40 | 1.0 | 52 |
| 14 | 330 | 22 | 76 | 4.6 | 10 |
| 15 | 341 | 22 | 74 | 1.7 | 12 |
| 16 | 304 | 20 | 53 | 1.5 | 37 |
| 17 | 320 | 23 | 62 | 1.7 | 26 |

Photopolymerization Conditions: 20 min. irradiation; >418 nm; 8.2 mW/cm$^2$

EXAMPLE 2

Selected TOSU/UVR-6105 formulations representing nine combinations of three different TOSUs (BOCHM, BCHEM, BMOCHM); three concentration levels (5, 10, 15 wt %); 1 PI (OPIA); one PS (CQ); one RP (EDMAB) and one temperature (37° C.) were subjected to PDSC analysis. The amounts of components in the various formulations are shown in Table 3.

TABLE 3

TOSU/UVR 6105 Photopolymerizable Compositions

| No. | Dioxirane | TOSU | TOSU Wt. % |
|---|---|---|---|
| 18 | UVR 6105 | None | 0 |
| 19 | UVR 6105 | BOCHM | 5 |
| 20 | UVR 6105 | BOCHM | 10 |
| 21 | UVR 6105 | BOCHM | 15 |
| 22 | UVR 6105 | BCHEM | 5 |
| 23 | UVR 6105 | BCHEM | 10 |
| 24 | UVR 6105 | BCHEM | 15 |
| 25 | UVR 6105 | BMOCHM | 5 |
| 26 | UVR 6105 | BMOCHM | 10 |
| 26 | UVR 6105 | BMOCHM | 15 |
| 28 | UVR 6105 | BMOCHM | 30 |

Note:
Photoinitiator System: OPIA/CQ/EDMAB = 1/0.5/0.1 wt %

A comparison of the composition and results of the PDSC data is summarized in Table 4. This data indicates that the presence of TOSU monomers only slightly reduce the exothermicity and the rate of all photo-reactions.

TABLE 4

TOSU/UVR 6105 Photopolymerization Characteristics at 37° C.

| No. | ΔH (J/g) | Ind. time (sec) | Peak max. (sec) | k (min$^{-1}$) |
|---|---|---|---|---|
| 18 | 215 | 10 | 17 | 0.22 |
| 19 | 158 | 11 | 20 | 0.23 |
| 20 | 185 | 11 | 20 | 0.18 |
| 21 | 149 | 12 | 22 | 0.16 |
| 22 | 116 | 11 | 21 | 0.97 |
| 23 | 182 | 13 | 25 | 0.42 |
| 24 | 160 | 15 | 28 | 0.38 |
| 25 | 135 | 11 | 19 | 0.31 |
| 26 | 170 | 9 | 17 | 1.10 |
| 27 | 163 | 13 | 23 | 0.28 |
| 28 | 140 | 20 | 37 | 0.14 |

Photopolymerization Conditions: 20 min. irradiation; >418 nm; 8.2 mWcm$^2$

EXAMPLE 3

Selected TOSU/UVR-6105/PTHF formulations representing 14 different combinations of two different TOSUs (BOCHM, BMOCHM) at seven concentration levels (0.5, 1, 5, 10, 15, 20, 25 wt %) and one TOSU (BCHEM) at three concentration levels (5, 10, 15 wt %) were prepared with other variables held constant: one PI (OPIA); one PS (CQ); one RP (EDMAB); one temperature (37° C.). The amounts of components in the various formulations are shown in Table 5.

TABLE 5

TOSU/UVR 6105/PTHF Photopolymerizable Compositions

| No. | Dioxirane | Wt. % | Polyol | Wt. % | TOSU | Wt. % |
|---|---|---|---|---|---|---|
| 29 | UVR 6105 | 80 | PTHF | 20 | None | 0 |
| 30 | UVR 6105 | 79.6 | PTHF | 19.9 | BOCHM | 0.5 |
| 31 | UVR 6105 | 79.2 | PTHF | 19.8 | BOCHM | 1 |
| 32 | UVR 6105 | 76 | PTHF | 19 | BOCHM | 5 |
| 33 | UVR 6105 | 72 | PTHF | 18 | BOCHM | 10 |
| 34 | UVR 6105 | 68 | PTHF | 17 | BOCHM | 15 |
| 35 | UVR 6105 | 64 | PTHF | 16 | BOCHM | 20 |
| 36 | UVR 6105 | 60 | PTHF | 15 | BOCHM | 25 |
| 37 | UVR 6105 | 76 | PTHF | 19 | BCHEM | 5 |
| 38 | UVR 6105 | 72 | PTHF | 18 | BCHEM | 10 |
| 39 | UVR 6105 | 68 | PTHF | 17 | BCHEM | 15 |
| 40 | UVR 6105 | 79.6 | PTHF | 19.9 | BMOCHM | 0.5 |
| 41 | UVR 6105 | 79.2 | PTHF | 19.8 | BMOCHM | 1 |
| 42 | UVR 6105 | 76 | PTHF | 19 | BMOCHM | 5 |
| 43 | UVR 6105 | 72 | PTHF | 18 | BMOCHM | 10 |
| 44 | UVR 6105 | 68 | PTHF | 17 | BMOCHM | 15 |
| 45 | UVR 6105 | 64 | PTHF | 16 | BMOCHM | 20 |
| 46 | UVR 6105 | 60 | PTHF | 15 | BMOCHM | 25 |

Note:
Photoinitiator System: OPIA/CQ/EDMAB = 1/0.5/0.1 wt %

The results of the PDSC analysis are shown in Table 6. These results indicate that increasing the concentration of TOSU up to about 10 wt % generally increases the exothermicity of reaction as indicated by heat of reaction (ΔH).

TABLE 6

TOSU/UVR 6105/PTHF Photopolymerization Characteristics at 37° C.

| No. | ΔH (J/g) | Ind. time (sec) | Peak max. (sec) | k (min$^{-1}$) |
|---|---|---|---|---|
| 29 | 249 | 10 | 18 | 10.8 |
| 30 | 288 | 12 | 24 | 9.2 |
| 31 | 273 | 11 | 21 | 7.0 |
| 32 | 258 | 11 | 21 | 6.8 |
| 33 | 307 | 9 | 20 | 9.3 |
| 34 | 274 | 11 | 28 | 7.1 |
| 35 | 261 | 10 | 28 | 7.0 |
| 36 | 144 | 16 | 53 | 1.2 |
| 37 | 264 | 14 | 25 | 8.3 |
| 38 | 300 | 15 | 32 | 5.2 |
| 39 | 280 | 13 | 32 | 5.8 |
| 40 | 178 | 7 | 19 | 5.1 |
| 41 | 309 | 11 | 20 | 9.9 |
| 42 | 312 | 12 | 20 | 10.6 |
| 43 | 327 | 10 | 16 | 10.4 |
| 44 | 298 | 10 | 18 | 10.8 |
| 45 | 235 | 23 | 42 | 5.8 |
| 46 | 263 | 17 | 36 | 7.7 |

Photopolymerization Conditions: 20 min. irradiation; >418 nm; 8.2 mW/cm$^2$

EXAMPLE 4

Selected TOSU/UVR-6105/PTHF formulations representing six different combinations of three different TOSUs (BOCHM, BCHEM, BMOCHM) at two concentration levels 10, 25 wt %) were prepared and tested with other variables held constant: one PI (OPIA); one PS (CQ); one RP (EDMAB); and one test temperature (60° C.). The amounts of components in the various formulations are shown in Table 7.

TABLE 7

TOSU/UVR 6105/PTHF Photopolymerizable Compositions

| No. | Dioxirane | Wt. % | Polyol | Wt. % | TOSU | Wt. 5 |
|---|---|---|---|---|---|---|
| 29 | UVR 6105 | 80 | PTHF | 20 | None | 0 |
| 33 | UVR 6105 | 72 | PTHF | 18 | BOCHM | 10 |
| 36 | UVR 6105 | 59.7 | PTHF | 14.9 | BOCHM | 25 |
| 43 | UVR 6105 | 72 | PTHF | 18 | BMOCHM | 10 |

TABLE 7-continued

TOSU/UVR 6105/PTHF Photopolymerizable Compositions

| No. | Dioxirane | Wt. % | Polyol | Wt. % | TOSU | Wt. 5 |
|---|---|---|---|---|---|---|
| 46 | UVR 6105 | 60 | PTHF | 15 | BMOCHM | 25 |
| 47 | UVR 6105 | 60 | PTHF | 16 | BMOCHM | 25 |

Note:
Photoinitiator System: OPIA/CQ/EDMAB = 1/0.5/0.1 wt %

The results of the PDSC analysis are shown in Table 8. These results demonstrate that addition of the TOSU monomer to the UVR-6105/PTHF base stock generally reduced the exothermicity and the rate of polymerization of the base stock.

TABLE 8

TOSU/UVR 6105/PTHF Photopolymerization Characteristics at 60° C.

| No. | ΔH (J/g) | Ind. time (sec) | Peak max. (sec) | k (min$^{-1}$) |
|---|---|---|---|---|
| 29 | 598 | 9 | 20 | 7.4 |
| 33 | 272 | 8 | 23 | 9.5 |
| 36 | 319 | 9 | 24 | 9.5 |
| 43 | 344 | 13 | 28 | 7.9 |
| 46 | 293 | 16 | 33 | 6.8 |
| 47 | 281 | 13 | 34 | 4.6 |

Photopolymerization Conditions: 20 min. irradiation; >418 nm; 8.2 mW/cm$^2$

EXAMPLE 5

The effect of irradiation time on the photoinitated homopolymerization of BMOCHM-TOSU monomer (20 wt % in methylene chloride) was evaluated by gel point determination and by FTIR spectroscopy. Selected IR absorption bands in the reaction mixture characteristic of hydroxyl, carbonyl and oxirane groups were monitored as a function of irradiation time. The results of the FTIR analysis are shown in Table 9. The results of the FTIR analysis shows: (a) growth in the hydroxyl band which may indicate oxirane, and or spiro ring opening; (b) growth in the carbonyl region which indicates spiro ring protonation and/or spiro ring opening; and (c) diminishment in the oxirane band indicating opening of the oxirane ring. These observations indicate the possibility of homopolymer formation. The mixture gelled 1.5 min post irradiation.

TABLE 9

Photoinitiated Solution Homopolymerization of BMOCHM-TOSU

| Irradiation | IR absorbance region $R_x/R_0$ ratio | | |
|---|---|---|---|
| time (min) | Hydroxyl 352–3418 cm$^{-1}$ | Carbonyl 1754–1744 cm$^{-1}$ | Oxirane 905 cm$^{-1}$ |
| 0.5 | 1.08 | 1.06 | 0.96 |
| 1 | 1.24 | 1.14 | 0.95 |
| 2 | 1.67 | 1.45 | 0.84 |
| 4 | 4.12 | 3.22 | 0.68 |
| 6 | 5.91 | 3.23 | 0.47 |
| 8 | 5.25 | 2.64 | 0.35 |

$R_x$ = [Band of Interest Absorbance/Reference Band Absorbance] at Time X
$R_0$ = [Band of Interest Absorbance/Reference Band Absorbance] at Time 0
Photoinitiator system: Gelest OMAN072/CQ/EDMAB = 3/1/0.1 wt %

TABLE 9-continued

Photoinitiated Solution Homopolymerization of BMOCHM-TOSU

| Irradiation | IR absorbance region $R_x/R_0$ ratio | | |
|---|---|---|---|
| time (min) | Hydroxyl 352–3418 cm$^{-1}$ | Carbonyl 1754–1744 cm$^{-1}$ | Oxirane 905 cm$^{-1}$ |

Polymerization: 20 wt % in methylene chloride; 26° C.; 3 M XL 2500 Dental Curing Lamp - 8 min; 923 mW/cm$^2$.

The effect of irradiation time on the photoinitiated solution copolymerization of an equimolar mixture of BMOCHM-TOSU monomer and EPON 825 (20 wt % in methylene dichloride) was analyzed by gel point determination and via an FTIR spectroscopic method. Selected IR absorption bands in the copolymerization mixture characterizatic of oxirane functionality in each of the monomers were monitored as a function of irradiation time. The results of these tests are shown in Table 10. The results clearly show: TOSU oxirane conversion proceeded at a faster rate and to a higher degree that EPON 825 oxirane conversion. Mixture gelled 1 min post irradiation. Growth in absorbance bands in the carbonyl and hydroxyl regions were similar to those observed during BMOCHM-TOSU homopolymerization.

TABLE 10

Photoinitiated Solution Copolymerization of BMOCHM-TOSU/EPON 825

| | Oxirane conversion (%) | |
|---|---|---|
| Irradiation time (min) | EPON 916 cm$^{-1}$ | BMOCHM-TOSU 905 cm$^{-1}$ |
| 1 | 3.1 | 5.5 |
| 2 | 4.5 | 10.6 |
| 3 | 4.3 | 14.0 |
| 4 | 4.9 | 14.9 |
| 5 | 8.3 | 21.8 |
| 6 | 11.9 | 26.7 |
| 7 | 12.8 | 26.9 |

% Conversion. = {[($A_{OX}/A_{REF}$) time 0 – ($A_{OX}/A_{REF}$) time 1]/($A_{OX}/A_{REF}$) time 0} × 100 where $A_{OX}$ = oxirane band absorbance; AREF = aromatic (1608 cm$^{-1}$) reference band absorbance.
Photoinitiator System: Gelest OMAN072/EDMAB = 3/1/0.1 wt %.
Photopolymerization: Equimolar mixture (20 wt %) in methylene chloride; 25° C.; 3M XL 2500 Dental Curing Lamp - 8 min; 899 mW/cm$^2$.

EXAMPLE 6

The solubility of seven structurally different TOSUs (DEODSH, DOTSHH, DEODSHX, DOTSHX, BOCHM, BOMOCHM, AND BCHEM) were determined at 25° C. in four different oxirane bases (BOCPE, BDDGE/PTHF, UVR 6105 and UVR 6105/PTHF). The results are summarized in Table 11. These results demonstrate that the DOTSHH TOSU which has a very rigid trispirocyclic structure is significantly less soluble than the other six TOSU with the less rigid, more flexible structures.

TABLE 11

Solubility of Selected TOSUs in Oxirane Coreactant Systems

| | | Oxirane base | | |
|---|---|---|---|---|
| TOSU | BOCPE | BDDGE/PTHF (80/20) | UVR 6105 | UVR 6105/ PTHF (80/20) |
| DEODSH[a] | >10 wt % | — | — | 40 wt % |
| DOTSHH[b] | 10 wt % | 5 wt % | — | <5 wt % |
| DEODSHX[a,e] | — | — | — | 30 wt 5 |
| DOTSHX[b,f] | <5 wt % | <5 wt % | — | — |
| BOCHM[c] | <10 wt % | — | 30 wt % | 25 wt % |
| BMOCHM[c] | <10 wt % | — | 30 wt % | 25 wt % |
| BCHEM[d] | — | — | 15–25 wt % | 25 wt % |

[a]fused-ring monooxirane
[b]fused-ring dioxirane
[c]flexible-linked fused-ring dioxirane
[d]unsaturated flexible-linked fused-ring
[e]5.5-diethyl-18-oxadispiro[1,3-dioxane-2,2'-1,3-dioxane-5'3"-bicyclo[3.1.0]hexane]
[f]6,24-dioxatrispiro[bicyclo[3.1.0]hexane-3.5'-1,3-dioxane-2.2'- 1,3-dioxane-5"3"'-bicyclo[3.1.0]hexane]

EXAMPLE 7

Formulations containing a TOSU (BOCHM, BMOCHM, or BCHEM), and a dioxirane (BOCPE or UVR 6105) or a dioxirane/polyol mixture (UVR 6105 and PTHF), were polymerized in bulk using a conventional dental curing light. The compositions tested and a description of the resultant products are given in Table 12. The photoinitiator system was OPIA/CQ/EDMAB 1/0.5/0.1 wt %. ~60 mg samples were placed in Teflon molds and irradiated at a distance of ~2 mm using a 3M XL3000 dental curing lamp (400 to 500 nm; ~500 mW/cm$^2$) for selected time periods (0.5 to 4 min). When possible, before products were fully cured, a post-irradiation FTIR spectrum was obtained to characterize the polymerizates. All products eventually cured to hard solids.

EXAMPLE 8

Figure 31:
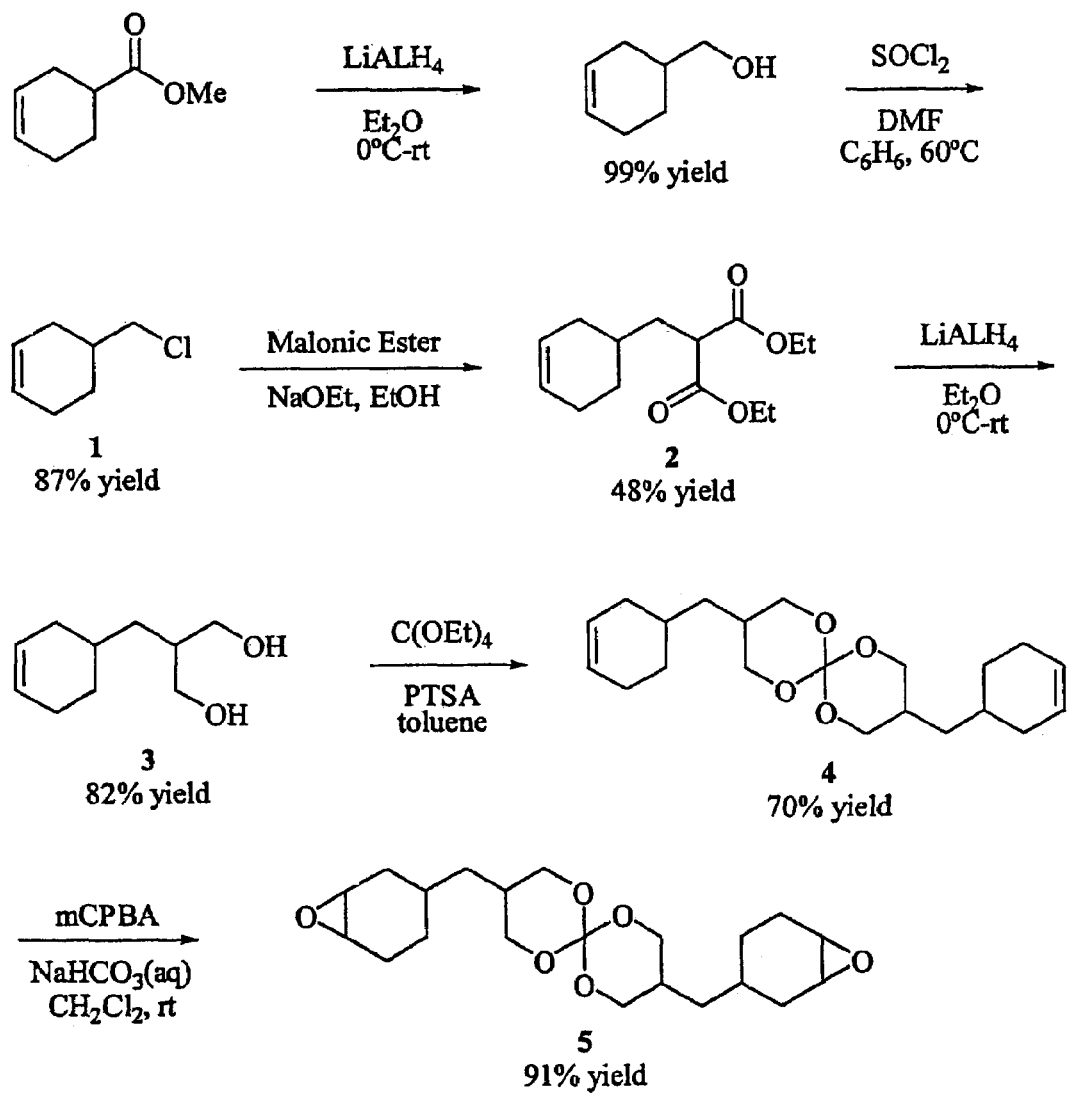
FIG. 31 is the synthesis scheme of 3,9-bis(cyclohex-3-enylmethyl)-1,5,7,11-tetraoxaspiro[5,5]undecane and 3,9-bis[(7-oxabicyclo[4.1.0]hept-3-yl)methyl]-1,5,7,11-tetraoxaspiro[5.5]undecane.

3,9-Bis(cyclohex-3-enylmethyl)-1,5,7,11-tetraoxaspiro[5.5]undecane (BCHEM) and 3,9-bis[(7-oxabicyclo[4.1.0]hept-3-yl)methyl]-1,5,7,11-tetraoxaspiro[5.5]undecane (BOCHM) were prepared. The synthetic sequence employed in the preparation of these diepoxy tetraoxaspiro[5.5]undecane is shown in FIG. 31. The diethyl malonate precursor of the coupling diol was prepared by methods known in the art.

To a flame-dried 2L round-bottomed flask were placed LiAlH4 (Aldrich, 95%, 29.03 g, 727 mmol) and anhydrous ethyl ether (10 mL). The resulting suspension was cooled to 0° C. with stirring. To this cold suspension was then added dropwise a solution of 3-cyclohexene -1-carbonxic acid methyl ester (TCI America, 97%, 100 g, 98 mL, 692 mmol) in ether (100 mL). Bubbles evolved during the course of addition. The resulting mixture was allowed to stir for an hour at 0° C. The cold bath was then removed, and the reaction mixture was allowed to stir for an additional 2 hours at room temperature. The reaction mixture was again cooled to 0° C., and the reaction was quenched by dropwise addition of methanol (10 mL). The resulting mixture was then slowly poured into a pre-cooled aqueous solution of saturated Rochelle salt (NaKC$_4$H$_4$O6.4H$_2$O, potassium sodium tartrate tetrahydrate, 1500 mL) at 0° C. The resulting mixture was allowed to stir while being slowly warmed to room temperature, and the metal gray solid became white. The aqueous phase was extracted with ethyl ether (4×750 mL). The organic phases were combined, washed with water (4×750 mL), dried over anhydrous Na$_2$SO$_4$, filtered and concentrated under reduced pressure to provide a colorless liquid which was shown to be fairly pure by GC (mainly one peak) and TLC (silica gel, 10% or 30% Et$^2$O/hexanes, mainly one spot) analyses. The crude material was subject to vacuum distillation and the desired alcohol, 3-cyclohexene-1-methanol, was collected as a colorless oil at 93-96° C./~20 mmHg in 99% yield. Bp (DSC) 204.44° C., 93-96° C./20 mmHg; $^1$H-NMR (CDCl$^3$, 300 MHz) δ 5.65 (m, 2H), 3.50-3.47 (dd, 2H, J=6, 2.4 Hz), 2.52-2.38 (m, 1H), 2.16-

TABLE 12

TOSU/UVR 6105/PTHF Bulk Photopolymerization Compositions and Products

| No. | Dioxirane | Wt. % | Polyol | Wt. % | TOSU | Wt. % | Solid product |
|---|---|---|---|---|---|---|---|
| 13 | BOCPE | 90 | None | 0 | BOCHM | 10 | clear; yellow |
| 17 | BOCPE | 90 | None | 0 | BMOCHM | 10 | clear; orange |
| 19 | UVR 6105 | 95 | None | 0 | BOCHM | 5 | clear; colorless |
| 20 | UVR 6105 | 90 | None | 0 | BOCHM | 10 | clear; colorless |
| 21 | UVR 6105 | 85 | None | 0 | BOCHM | 15 | clear; colorless |
| 22 | UVR 6105 | 95 | None | 0 | BCHEM | 5 | clear; colorless |
| 23 | UVR 6105 | 90 | None | 0 | BCHEM | 10 | clear; colorless |
| 24 | UVR 6105 | 85 | None | 0 | BCHEM | 15 | clear; colorless |
| 32 | UVR 6105 | 76 | PTHF | 19 | BOCHM | 5 | clear; colorless |
| 33 | UVR 6105 | 72 | PTHF | 18 | BOCHM | 10 | clear; pale yellow |
| 34 | UVR 6105 | 68 | PTHF | 17 | BOCHM | 15 | clear; colorless |
| 37 | UVR 6105 | 76 | PTHF | 19 | BOCHM | 5 | clear; pale yellow |
| 38 | UVR 6105 | 72 | PTHF | 18 | BOCHM | 10 | clear; colorless |
| 39 | UVR 6105 | 68 | PTHF | 17 | BCHEM | 15 | clear; colorless |
| 42 | UVR 6105 | 76 | PTHF | 19 | BMOCHM | 5 | clear; pale yellow |
| 43 | UVR 6105 | 72 | PTHF | 18 | BOCHM | 10 | clear; colorless |
| 44 | UVR 6105 | 68 | PTHF | 17 | BMOCHM | 15 | clear; pale yellow |

Note:
Photoinitiator System: OPIA/CQ/EDMAB = 1/0.5/0.1 wt 5%
Photopolymerization Conditions: ~60 mg sample in Teflon mold; 3 M XL3000 curing light 400–500 mm; ~500 mW/cm$^2$; selected irradiation times; 2 mm distance; final cure upon standing at R. T.).

1.99 (m, 3H), 1.84-1.64 (m, 3H), 1.32-1.26 (m, 1H); $^{13}$C-NMR (CDCl$^3$, 300 MHz) δ 126.98, 125.79, 67.47, 36.11, 27.99, 25.11, 24.49; FT-IR (neat) (cm$^{-1}$) 3310, 3019, 2913, 2835, 1652, 1434, 1260, 1188, 1140, 1091, 1024, 966, 937, 738, 729, 651.

To a flame-dried three-necked 1L round-bottomed flask equipped with a magnetic stir bar, a condenser, a dropping funnel, and a thermometer was placed a mixture of thionyl chloride (Aldrich, 99+%, 41.26 mL, 67.3 g, 560 mmol), benzene (100 mL) and N,N-dimethylformamide (Aldrich, anhydrous 4 drops). To this mixture at room temperature was added dropwise a solution of 3-cyclohexene-1-methanol (44.87 g, 400 mmol) in benzene (200 mL) through the dropping funnel over a period of 90 minutes (bubbles evolved). The resulting mixture was then brought to 60° C. and maintained at this temperature for an additional 4 hours (a lot more bubbles). The reaction mixture was allowed to slowly cool to room temperature and stirred overnight. The mixture was transferred to a 1L round-bottomed flask, and the solvent along with volatile by-products were removed under reduced pressure. The light yellow residue liquid was subject to vacuum distillation, and the desired product, 3-cyclohexene-1-chloromethane, was collected at 58-60° C./~20 mmHg as a colorless liquid in 87% yield. (The colorless chloride compound turned brownish yellow over a period of 5 days). Bp 58-60° C./20 mmHg; $^1$H-NMR (CDCl$^3$, 300 MHz) δ 5.67 (m, 2H), 3.48-3.45 (d, 2H, J=6.3 Hz), 2.26-1.76 (m, 6H), 1.44-1.30 (m, 1H); $^{13}$C-NMR (CDCl$^3$, 300 MHz) δ 126.88, 125.26, 50.07, 36.14, 29.24, 26.27, 24.51; FTIR (neat) (cm$^{-1}$) 3019, 2913, 2835, 1657, 1434, 1309, 1260, 1140, 1043, 917, 743, 719, 651.

Sodium ethoxide (NaOEt) was prepared in situ as follow: To a flame-dried three-necked 500 mL round-bottomed flask equipped with a magnetic stir bar, a condenser, a dropping funnel, and a thermometer were placed sodium metal (6.90 g, 300 mmol) and anhydrous ethanol (160 mL). The mixture was allowed to react at room temperature with stirring until all the sodium metal was consumed.

The above in-situ generated sodium ethoxide solution was brought to 70° C. and then diethyl malonate (Aldrich, 99%, 46 mL, 300 mmol) was added dropwise through the dropping funnel over a period of 30 minutes. The resulting mixture was allowed to stir at 70° C. for an additional 30 minutes after the completion of the malonate addition. To this mixture was then added dropwise a solution of 3-cyclohexene-1-chloromethane (39.19 g, 300 mmol) in absolute ethanol (100 mL) through the dropping funnel over a period of 45 minutes. The resulting mixture was brought to reflux (white solid formed after 30 minutes of refluxing) after the completion of addition and was maintained at reflux temperature for 24 hours while monitored by TLC (silica gel, 20% Et$^2$O/hexanes). The reaction mixture was allowed to cool to room temperature, and the solvent was removed under reduced pressure. The residue was taken up with a mixture of water (450 mL) and diethyl ether (100 mL). The aqueous phase was separated and extracted with diethyl ether (3×350 mL). The combined organic phase was dried over anhydrous magnesium sulfate, filtered, and concentrated under reduced pressure to provide a light yellow liquid product (62.06 g, 81.35% crude yield). The crude material was subject to vacuum distillation and the desired diethyl 2-(3-cyclohexene-1-methyl)malonate was collected at 145-147° C./0.75 mmHg as a colorless liquid in 48% yield. Bp 145-147° C./0.75 mmHg; $^1$H-NMR (CDCl$^3$, 300 MHz) δ 5.59 (m, 2H)m, 4.18-4.10 (q, 4H, J=7.2 Hz), 3.44-3.37 (t, 1H, J=7.8 Hz), 2.13-1.40 (m, 9H), 1.22 (t, 6H, J=7.2Hz); $^{13}$C-NMR (CDCl$^3$, 300 MHz) δ 169.50, 126.82, 125.71, 61.16, 49.54, 35.14, 31.32, 31.21, 28.34, 24.77, 13.93; FTIR (neat) (cm$^{-1}$) 3019, 2981, 2913, 1749, 1729, 1444, 1367, 1304, 1270, 1236, 1193, 1149, 1096, 1028.

To a flame-dried 1 L round-bottomed flask was placed a mixture of lithium aluminum hydride powder (Aldrich, 95%, 9.98 g, 249.7 mmol) and anhydrous diethyl ether (200 mL). The mixture was allowed to stir while cooling to 0° C. To this cold LAH suspension was then added dropwise a solution of diethyl 2-(3'-cyclohexene-1'-methyl)malonate (25.20 g, 103 mmol) in anhydrous diethyl ether (50 mL) through a dropping funnel over a period of 30 minutes. The resulting mixture was allowed to stir for an hour at 0° C. and then slowly warmed to room temperature. The reaction mixture was allowed to stir at room temperature for an additional 3 hours. The reaction mixture was then diluted with diethyl ether (250 mL), cooled to 0° C., and quenched by dropwise addition of methanol (25 mL). The resulting mixture was allowed to stir for 30 minutes and then slowly poured into an aqueous solution of saturated Rochelle salt (500 mL) at 0° C. The resulting mixture was allowed to stir while it slowly came to room temperature and the gray metal solid became white. The aqueous layer was separated and extracted with diethyl ether (2×700 mL). The combined organic phase was washed with water (2×750 mL), dried over anhydrous sodium sulfate, filtered and concentrated under reduced pressure to give a white solid (95.5% crude yield) which was shown to be a mixture of 4 components by GC analysis. The crude material was purified by recrystallization from diethyl ether/hexanes (1/4 v/v). The desired 2-(3-cyclohexene-1-methyl)-1,3-propanediol was obtained as white needle crystalines in 82% yield. Mp (DSC) 86.9° C.; $^1$H-NMR (CDCl$^3$, 300 MHz) δ 5.65 (m, 2H), 3.89-3.76 (m, 2H), 3.68-3.61 (m, 2H), 2.76 (s, 2H), 2.18-1.86 (m, 4H), 1.79-1.53 (m, 3H), 1.28-1.11 (m, 3H); $^{13}$C-NMR (CDCl$^3$, 300 MHz) δ 127.06, 126.18, 66.97, 66.70, 38.74, 34.44, 32.02, 30.74, 29.05, 25.08; FTIR (KBr pellet) (cm$^{-1}$) 3291, 3019, 2903.

Figure 32:
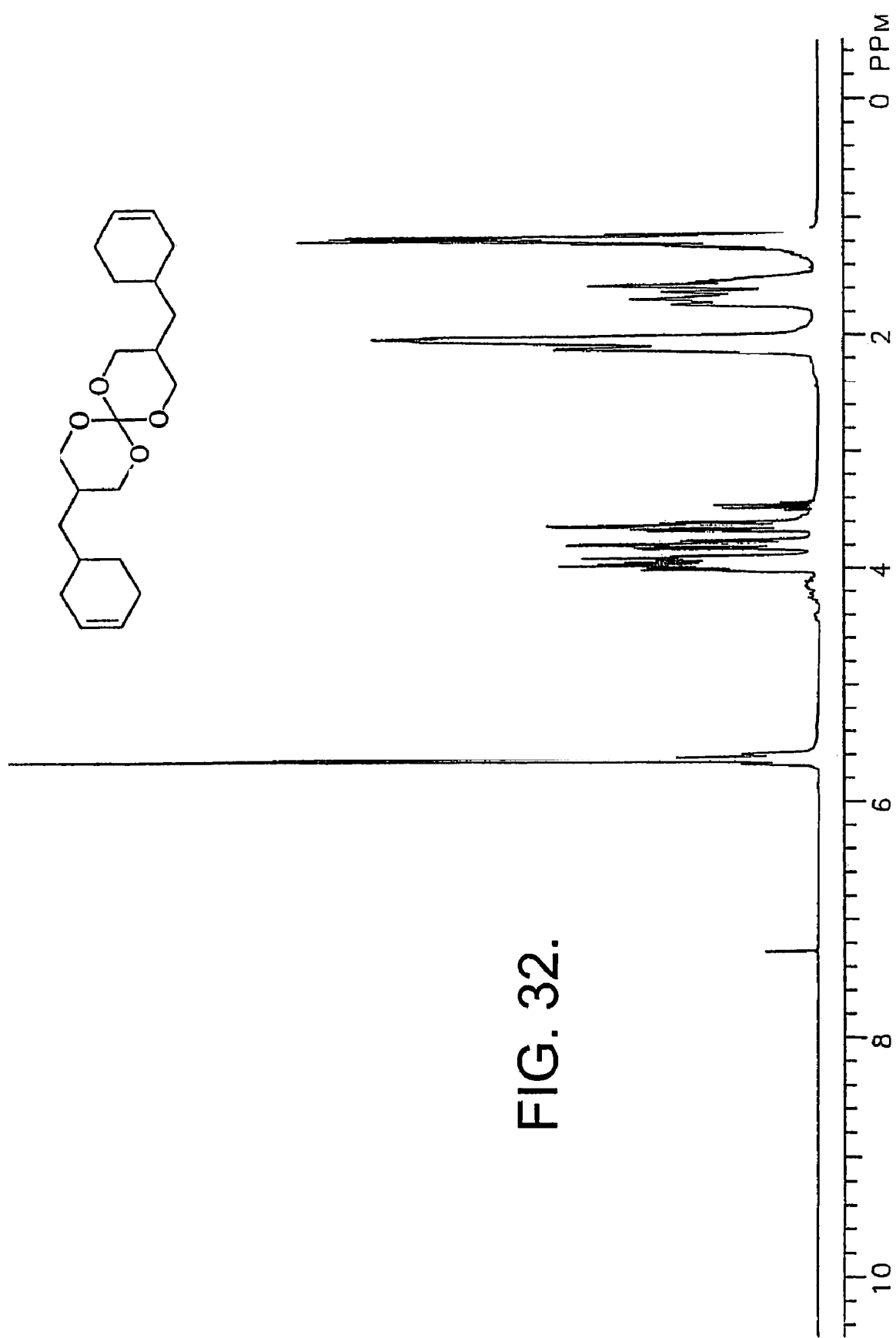
FIG. 32 is the $^1$H-NMR spectrum of 3,9-bis(cyclohex-3-enylmethyl)-1,5,7,11-tetraoxaspiro[5,5]undecane.
Figure 33:
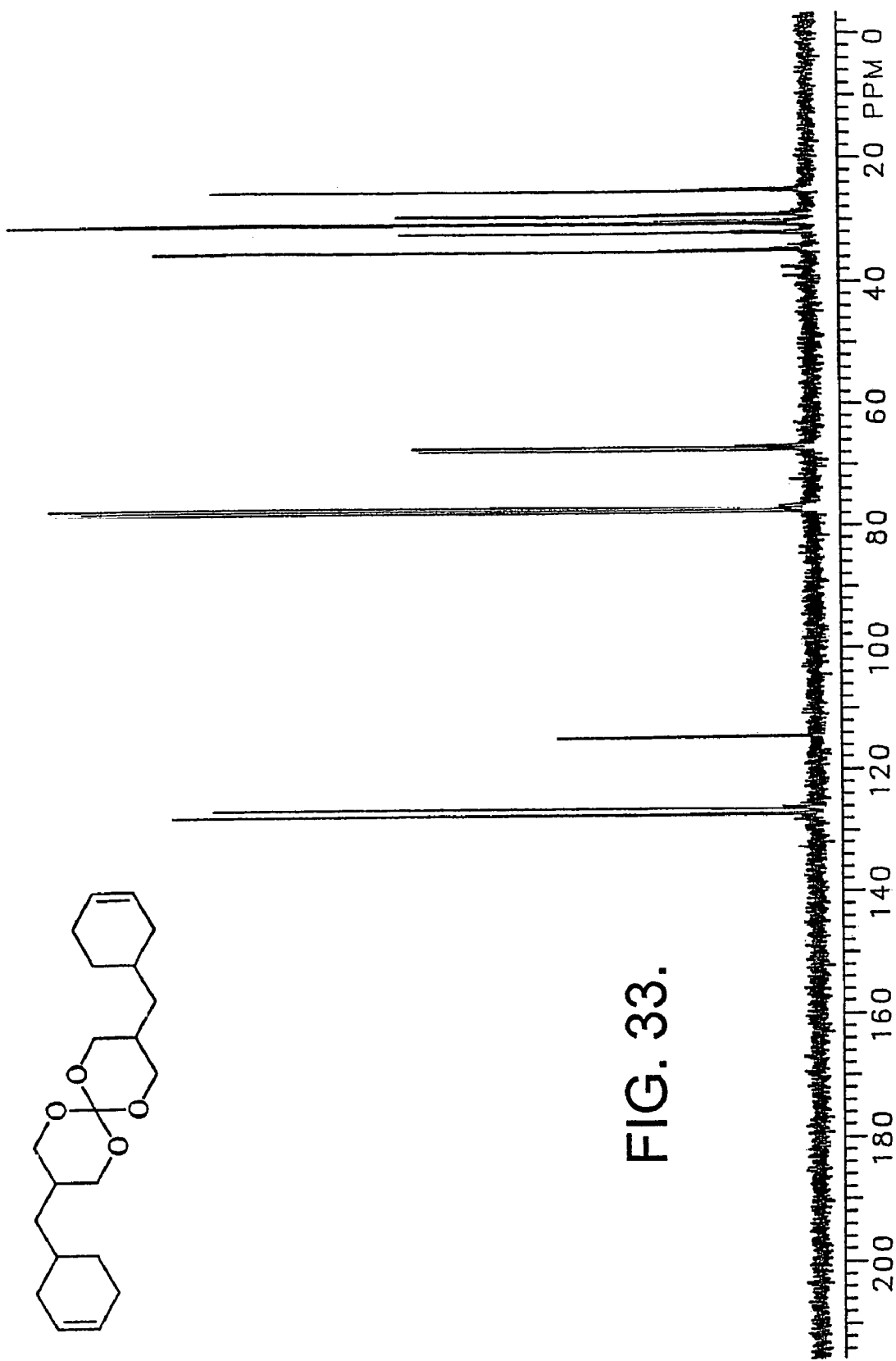
FIG. 33 is the $^1$C-NMR spectrum of 3,9-bis(cyclohex-3-enylmethyl)-1,5,7,11-tetraoxaspiro[5,5]undecane.
Figure 34:
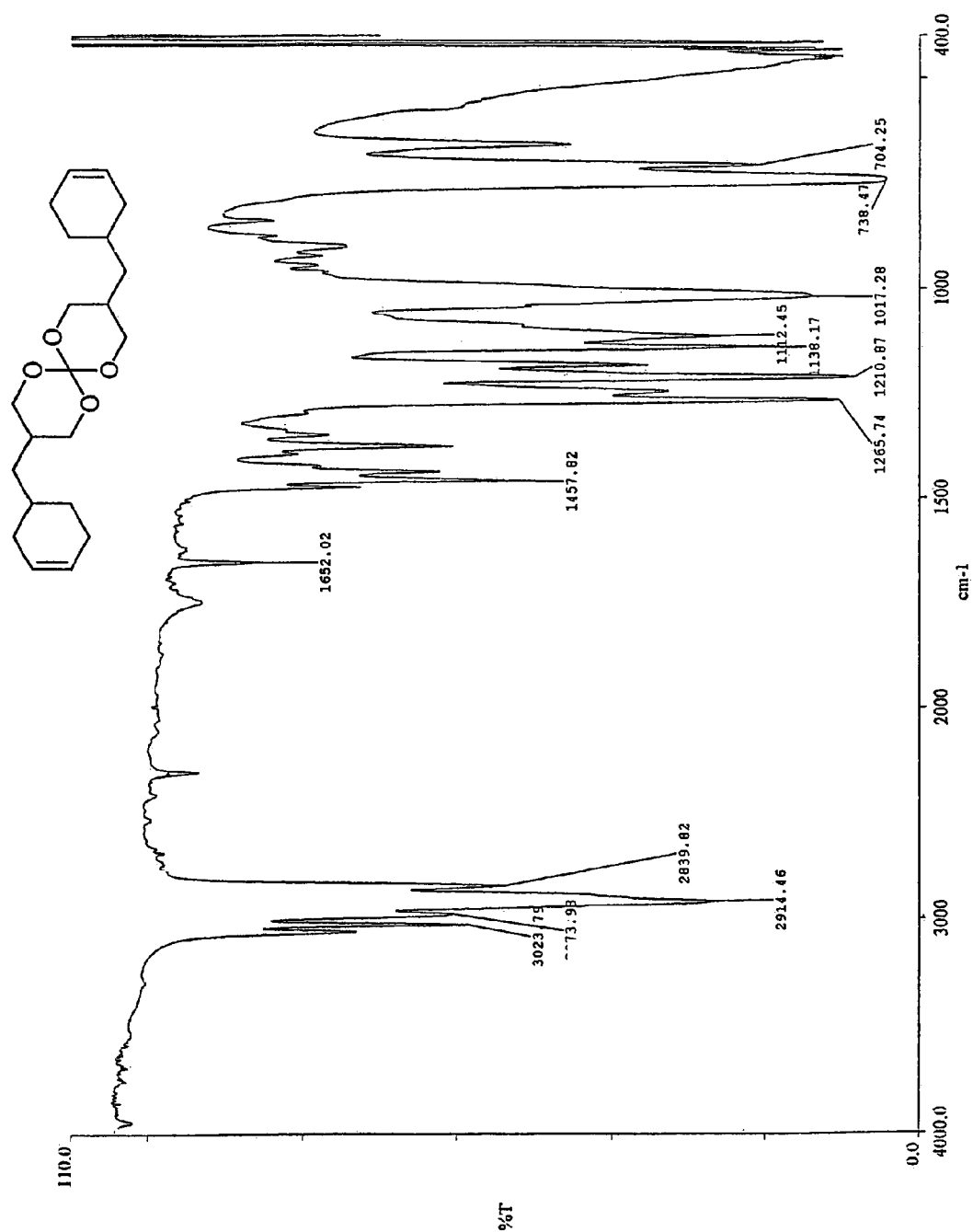
FIG. 34 is the FTIR spectrum of 3,9-bis[(3'cyclohexenyl)methyl]1,5,7,11-tetraoxaspiro[5.5]undecane.

To a three-necked 500 mL round-bottomed flask equipped with a magnetic stir bar, a Dean-Stark trap, a condenser and a thermometer was placed a mixture of toluene (300 mL) and 2-(3-cyclohexene-l-methyl)-1,3-propanediol (13.62 g, 80 ml). The starting diol solid did not dissolve in toluene until it was heated up to 45° C. The solution was maintained at reflux for an hour and 25 mL of azeotropical mixture was removed from the Dean-Stark trap. The mixture was allowed to cool to room temperature and then anhydrous p-toluene sulphonic acid (PTSA, 0.23 g) was added, followed by the addition of tetraethyl orthocarbonate (TEOC, 8.4 mL, 40 mmol). The resulting mixture was then brought to reflux to azeotropically remove, through the Dean-Stark trap, the by-product ethanol thus formed during the reaction. The azeotropic mixture was shaken with salty water to determine the amount of ethanol collected. After removing 180 mL of the azeotropic mixture, the reaction mixture was maintained at ~108° C. overnight. The reaction mixture was allowed to cool to room temperature (no solid precipitated) and then triethylamine (1.5 mL) was added. The resulting mixture was allowed to stir for a half hour, transferred to a 500 mL round-bottomed flask and concentrated under reduced pressure to give a white solid, which was not soluble in diethyl ether but was soluble in methylene chloride. The crude material was purified by recrystallization from boiling diethyl ether. The desired product 3,9-bis[(3-cyclohexenyl) methyl]-1,5,7,11-tetraoxaspiro[5.5]undecane was obtained as white crystals in 70% yield. Mp (DSC) 100.83° C.; $^1$H-NMR (CDCl$^3$, 300 MHz) δ 5.63 (s, 4H), 4.20-3.87 (m, 4H), 3.84-3.74 (dt, 2H, J=9.6, 3.9 Hz), 3.68-3.59 (dt, 2H, J=9.6, 3.9 Hz), 2.18-1.98 (m, 8H), 1.78-1.46 (m, 6H), 134-1.08 (m, 6H); $^{13}$C-NMR (CDCl$^3$, 300 MHz) δ 127.00, 125.98, 114.35, 67.33, 67.17, 66.79, 66.63, 34.72, 31.84, 31.81, 30.39, 30.05, 28.94, 28.89, 24.94; FTIR (evaporation of CDCl$^3$ solution) (cm$^{-1}$) 3056, 3024, 2974, 2840, 1652, 1458, 1436, 1376, 1266, 1244, 1211, 1182, 1138, 1112, 704, 656; Anal. Calcd. for $C_{21}H_{32}O_4$: C, 72.38; H, 9.26; Found: C, 72.43; H, 9.54. The $^1$H-NMR Spectrum, the $^1$C-NMR Spectrum, and the FTIR Spectrum of 3,9-bis[(3'cyclohexenyl)methyl]1,5,7,11-tetraoxaspiro[5.5]undecane (BCHEM) are shown in FIGS. 32-34, respectively.

Figure 35:
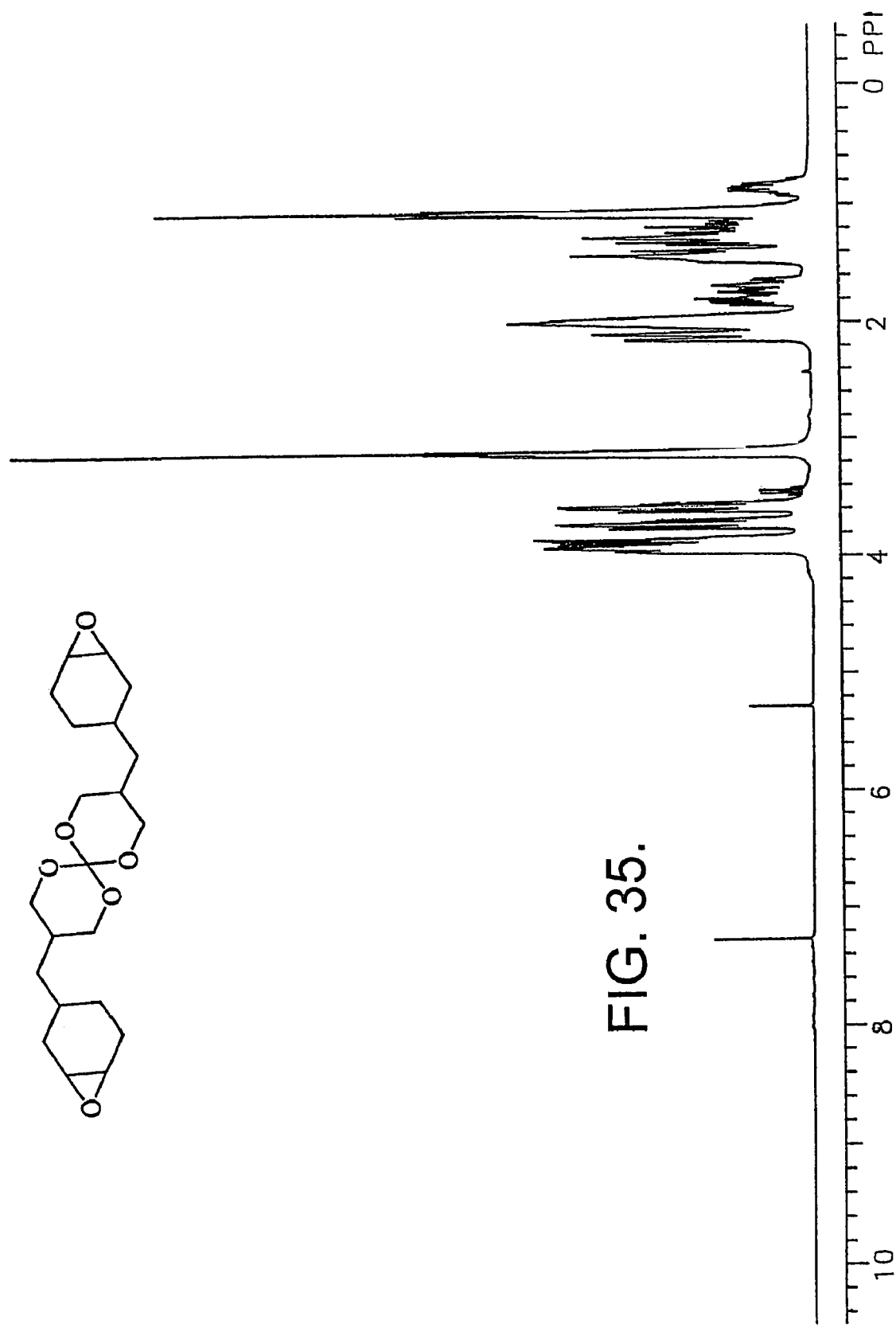
FIG. 35 is the $^1$H-NMR spectrum of 3,9-bis(cyclohex-3-enylmethyl)-1,5,7,11-tetraoxaspiro[5,5]undecane.
Figure 37:
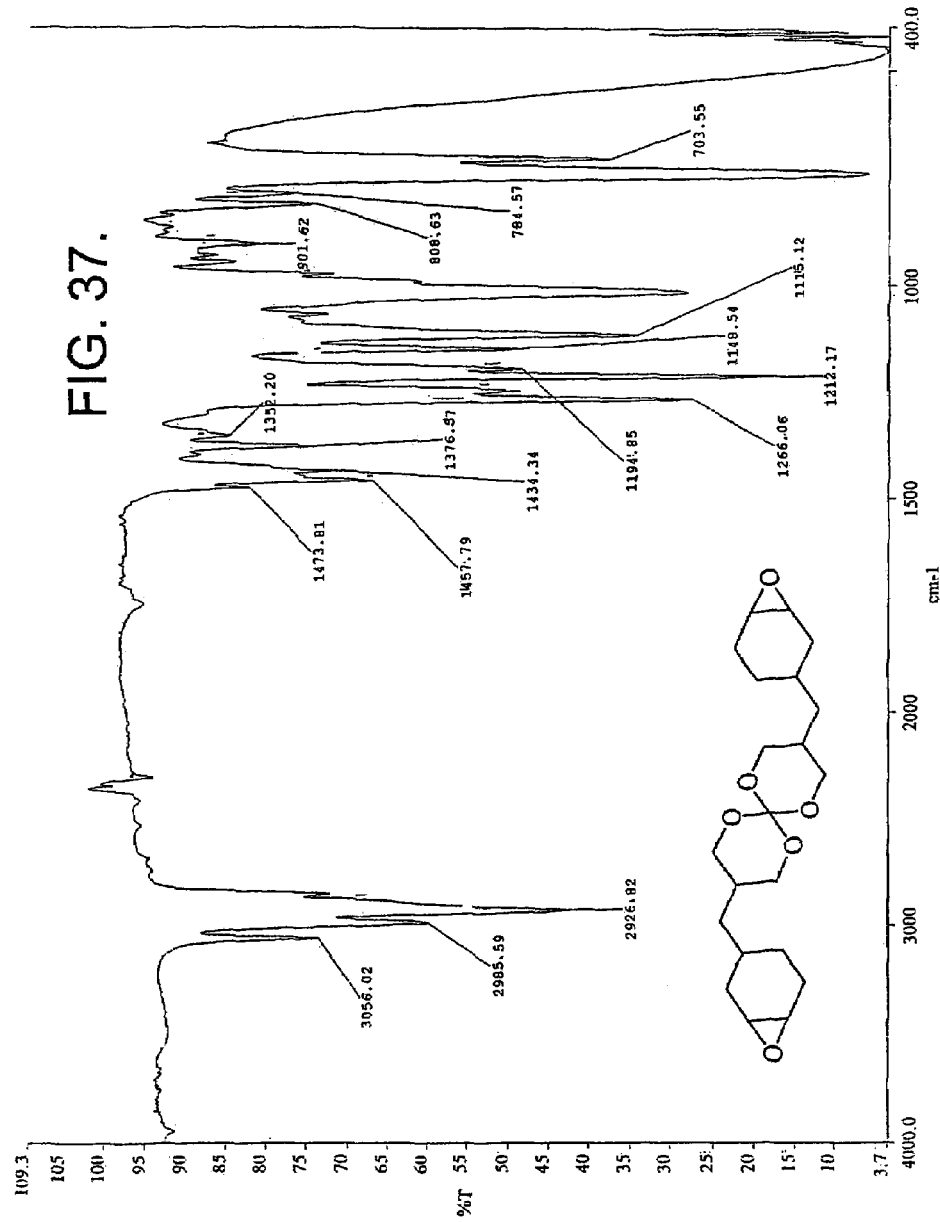
FIG. 37 is the FTIR spectrum of 3,9-bis(cyclohex-3-enylmethyl)-1,5,7,11-tetraoxaspiro[5,5]undecane.

3,9-Bis[(7-oxabicyclo[4.1.0]hept-3-yl)methyl]1,5,7,11-tetraoxaspiro[5.5]undecane (BOCHM) was prepared employing biphasic epoxidation due to the acid sensitive nature the compound. To a 500 mL round-bottomed flask was placed a mixture of 3,9-bis[(3-cyclohexenyl)methyl]-1,5,7,11-tetraoxaspiro[5.5]undecane (BCHEM-TOSU 4, 3.48 g, 10 mmol) and 150 mL of methylene chloride (CH$_2$Cl$_2$). To this solution was added 0.5 M aqueous solution of sodium bicarbonate (62 mL, pH ~8). The resulting biphasic mixture was allowed to stir vigorously at room temperature and then m-chloroperbenzoic acid (Aldrich, 77% max., mCPBA, 4.53 g, ~20.2 mmol) was slowly added in several portions over a period of 30 minutes. The resulting mixture was allowed to stir for an additional 5 hours at room temperature, and the reaction progress was monitored by TLC (silica gel, 25% ether/hexanes). The two phases were separated, and the organic phase was washed successively with 1 N aqueous NaOH 92×75 mL) and water (2×75 mL). The combined aqueous phase was back extracted with methylene chloride (2×100 mL). The organic phases were combined, dried over anhydrous Na$_2$SO$_4$, and concentrated under reduced pressure to give a white solid. The crude material was washed with 5 mL of cold ether (pre-cooled at 0° C.) and purified by flash chromatography (silica gel, 15% ethyl ether/hexanes) or by recrystallization two times from diethyl ether/hexanes (the crude material was dissolved in refluxing ether, allowed to cool to room temperature and then hexanes were slowly added). The desired product BOCHM-TOSU was obtained as white crystals in 91% yield. Mp (DSC) 110.56°, (capillary) 105-106° C.; $^1$H-NMR (CDCl$^3$, 300 MHz) δ 3.98-3.82 (m, 4H), 3.76-3.67 (dt, 2H, J=9.5, 3.9 Hz), 3.62-3.52 (dt, 2H, J=9.5, 3.9 Hz), 3.16-3.06 (m, 4H), 2.17-1.92 9m, 6H), 1.86-1.62 (m, 2H), 1.50-0.98 (m, 11H), 0.93-0.77 (m, 1H); $^{13}$C-NMR (CDCl$^3$, 300 MHz) δ 114.26, 67.08, 67.03, 66.88, 66.59, 66.52, 66.48, 66.44, 52.84, 52.34, 51.67, 51.39, 34.98, 34.95, 34.49, 32.00, 31.94, 30.77, 30.65, 29.89, 29.85, 29.56, 27.21, 26.45, 24.99, 24.56, 24.42, 23.34; FTIR (evaporation of CDCl$^3$, solution) (cm$^{-1}$) 3056, 2986, 2927, 1474, 1458, 1434, 1377, 1266, 1212, 1195, 1149, 1115, 902, 809, 785, 704; Anal. Calcd. for $C_{21}H_{32}O_6$: C, 66.29; H, 8.48; Found: C, 66.03; H, 8.64. The $^1$H-NMR Spectrum, the $^1$C-NMR Spectrum, and the FTIR Spectrum of 3,9-bis[(7-oxabicyclo[4.1.0]hept-3-yl)methyl]1,5,7,11-tetraoxaspiro[5.5]undecane (BOCHM) are shown in FIGS. 35-37, respectively.

EXAMPLE 9

Figure 38:
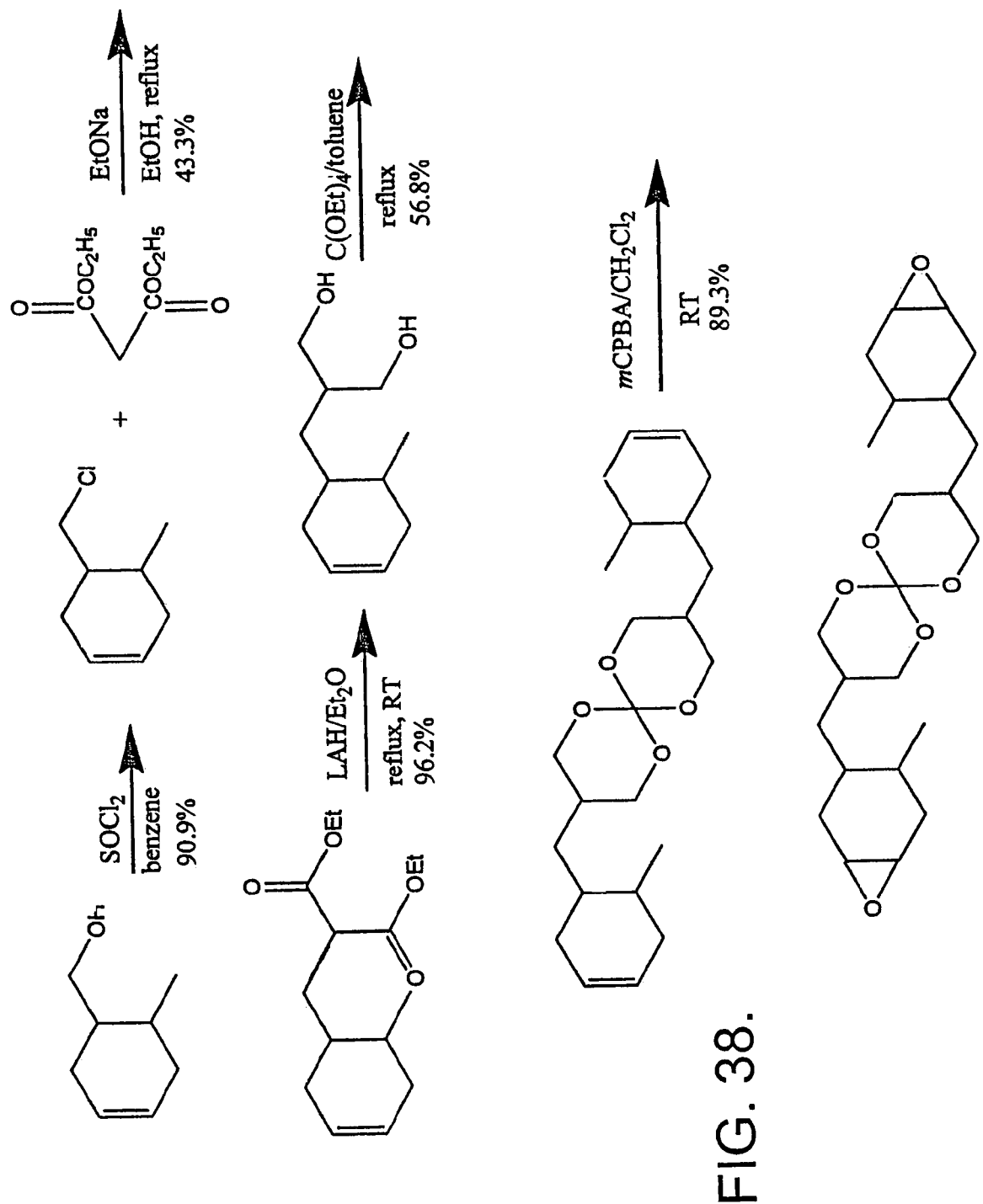
FIG. 38 is the synthesis scheme of 3,9-bis[(6-methylcyclohex-3-enyl)methyl]-1,5,7,11-tetraoxaspiro[5,5]undecane and 3,9-bis[(4-methyl-7-oxabicyclo[4.1.0]hept-3-yl)methyl]-1,5,7,11-tetraoxaspiro[5,5]undecane.

3,9-Bis[(6-methylcyclohex-3-enyl)methyl]-1,5,7,11-tetraoxaspiro[5.5]undecane (BMCHEM) and 3,9-bis[(4-methyl-7-oxabicyclo[4.1.0]hept-3-yl)methyl]-1,5,7,11-tetraoxaspiro[5.5]undecane (BMOCHM) were prepared. The synthetic sequence employed in the preparation of this diepoxy spiroorthocarbonate is shown in FIG. 38.

The following chloro-, -diacetate, -diol cyclohexene compounds were prepared as follows: To an oven dried three-necked round bottomed 500 mL flask, equipped with an additional funnel, a reflux condenser, a thermometer, a magnetic stirrer bar and a cooling bath, and blanketed with N$_2$ was charged with (1) 1-hydroxymethyl-6-methyl-3-cyclohexene 40.9 mL (Aldrich, 97%, 0.30 mole) in 150 mL benzene along with a few drops of anhydrous N,N-dimethylformamide. To this stirred solution thionyl chloride 31.0 mL (Aldrich, 99%, 0.42 mole) in 75 mL benzene was then added dropwise from the additional funnel. Not much exotherm was observed, although maintaining the reaction mixture at about 15° C. was preferred due to much gas evolution. Upon completion of addition, the cooling bath was removed, and the reaction mixture was slowly brought up to and stirred at 60° C. for two more hours while the color of the mixture turned from colorless to light amber to reddish brown. TLC (silica gel, ethyl ether/hexanes 1/1, V/V) showed the starting material (Rf 0.33) had almost disappeared and a new spot (Rf 0.7) formed. The reaction mixture was stripped of volatile compounds under reduced pressure and distilled in a 4" Vigreaux column to produce the colorless liquid of a mixture of diastereomers of 1-chloromethyl-6-methyl-3-cyclohexene 39.5 g at 82-3° C./20 mmHg (yield 90.9%). $^1$H-NMR (CDCl$^3$, 300 MHZ) δ 5.62-5.60 (m, 2H) 3.63-3.61 (m, 2H), 2.14-2.09 (m, 4H), 1.80-1.75 (m, 3H), 1.00-0.98, 0.88-0.86 (dd, 3H, J=6.0 Hz); $^{13}$C-NMR (CDCl$^3$, 300 MHZ) δ 126.01, 125.50, 124,59, 48.62, 46.93, 41.08, 39.78, 33.04, 32.26, 29.86, 28.50, 28.35, 26.42, 18.86, 14.19; FT-IR (neat, cm$^{-1}$) 3026, 2958, 2897, 2839, 1657, 1436, 1378, 1294, 1154, 1007, 891, 776, 723, 658; GC (Acetone; detector 300° C., injector 270° C., column: 60° C. 12 min., 20° C./min to 260° C. 5 min) (showed 1 peak at 7.1 min.) Anal. Calcd for $C_8H_{13}Cl$: 66.43; H, 9.06; Found: C,; H.

An oven dried three-necked round bottomed 500 mL flask, equipped with an additional funnel, a reflux condenser, a thermometer, a magnetic stirrer bar and a cooling bath, and blanketed with N$_2$ was charged with anhydrous ethanol 190 mL. Sodium 8.61 g (Aldrich, 0.3745 mole) was then added in small pieces over a period of one hour. Upon completion of addition, the cooling bath was removed, and the mixture was heated to 70° C. 1-Chloromethyl-6-methyl-3-cyclohexene was then added. The reaction mixture was stirred for another 30 min, was brought up to reflux for 9 hours and left stirring overnight. The reaction was monitored with TLC (silica gel, Et$^2$O/hexanes ½, V/V). Then, ethanol was mostly removed under reduced pressure, and water and ethyl ether were added to dissolve the resultant mixture. The organic phase was thus separated from the aqueous phase and washed with water 3×200 mL until the pH reached 7. The aqueous phase was back extracted with ether, and the extraction was washed with water to obtain pH 7. The washed organic phases were combined and dried over anhydrous MgSO$_4$ and was filtered and concentrated under reduced pressure. This resultant mixture was distilled to give 43.6 g of the colorless oil of 1-(6-methyl-3-cyclohexene)-2-methyl-propanediacetate at 155-7° C./6-7 mmHg (yield 43.3%). $^1$H-NMR (CDCl$^3$, 300 MHZ) δ 5.60-5.50 (m, 2H), 4.19-4.11 (m, 4H), 3.44-3.38 (m, 1H), 2.24-2.10 (m, 3H), 1.67-1.58 (M, 4H), 1.25-1.19 9d, d, d, 6H, J=3.9 Hz), 0.96-0.92 (d, d, 3H, J=3.9 Hz); $^{13}$C-NMR (CDCl$^3$, 300 MHZ) δ 169.77, 169.36, 126.08, 125.19, 61.23, 61.10, 49.67, 36.68, 32.86, 32.52, 32.38, 29.46, 19.38, 13.98; FT-IR (neat, cm$^{-1}$) 3024, 2980, 2905, 2832, 1733, 1657, 1445, 1369, 1250, 1193, 1151, 1031, 853, 664; GC (Et$^2$O; detector 300° C., injector 270° C., column: 60° C. 5 min, 20°

C./min to 260° C. 7 min) (showed 1 peak @ 10.1 min.); Anal. Calcd. for $C_{15}H_{24}O_4$: C, 67.14; H 9.01; Found: C, 66.95; H, 9.27.

An oven dried three-necked round bottomed 500 mL flask, equipped with an additional funnel, a reflux condenser, a thermometer, a magnetic stirrer bar and a cooling bath, and blanketed with $N_2$ was charged with anhydrous diethyl ether 220 mL and lithium aluminum hydride, LAH 7.73 g (Aldrich, 95%, 0.1936 mole). To this suspension 1-(6-methyl-3-cyclohexene)-2-methyl-propanediacetate (3) was added dropwise while maintaining a temperature of 3-5° C. Upon completion of addition, the reaction mixture was stirred for an additional hour at this temperature. Then it was brought up to reflux at 32-35° C. for 2 hours followed by stirring at room temperature overnight. The reaction was monitored with TLC (silica gel, $Et^2O$/hexanes 1.5/1, V/V). The starting material (Rf 0.68) had disappeared and a new spot Rf 0.05 was observed. A saturated aqueous Rochelle salt 450 mL and methanol 32 mL were then added to get rid of the excess LAH. Water was added to separate the organic phases from the slightly opaque aqueous phase. The organic phase was washed with 3×100 mL of water until the pH reached 7. The aqueous phase was back extracted with 4×200 mL $Et^2O$ and was washed with water until the pH reached 7. The organic phases were combined, dried over $MgSO_4$, filtered and concentrated under reduced pressure to give a crude product. The latter was purified by flash chromatography (silica gel, ethyl acetate/hexanes ½ to 1/0) to obtain the colorless oil of 1-(6-Methyl-3-cyclohexane)-2-methylene-propanediol 11.0 g (96.2% yield). $^1$H-NMR (CDCl$^3$, 300 MHZ) δ 5.65-5.55 (m, 2H), 3.83-3.55 (m, 2H), 3.30 (s, 2H), 2.82-2.04 9m, 2H), 1.87-1.86 (m, 1H), 1.68-1.63 (m, 2H), 1.51-1.43 (m, 2H), 1.33-1.31 (m, 1H), 0.94-0.92 (m, 3H); 13C-NMR (CDCl$^3$, 300 MHZ) 6 126.14, 125.57, 67.41, 65.53, 38.88, 36.07, 32.89, 32.79, 31.38, 30.3, 19.60; FT-IR (neat, cm$^{-1}$) 3324, 3022, 2961, 2903, 2880, 2825, 1660, 1463, 1443, 1377, 1030, 969, 659; GC (($Et^2O$; detector 300° C., injector 270° C., column: 60° C. 5 min, 20° C./min to 260° C. 7 min) (showed 2 peaks @ 12.1, 7.0 min.); Anal. Calcd. For $C_{11}H_{20}O_2$: C, 71.70, H, 10.94; Found: C, 71.26; H, 11.35.

Figure 39:
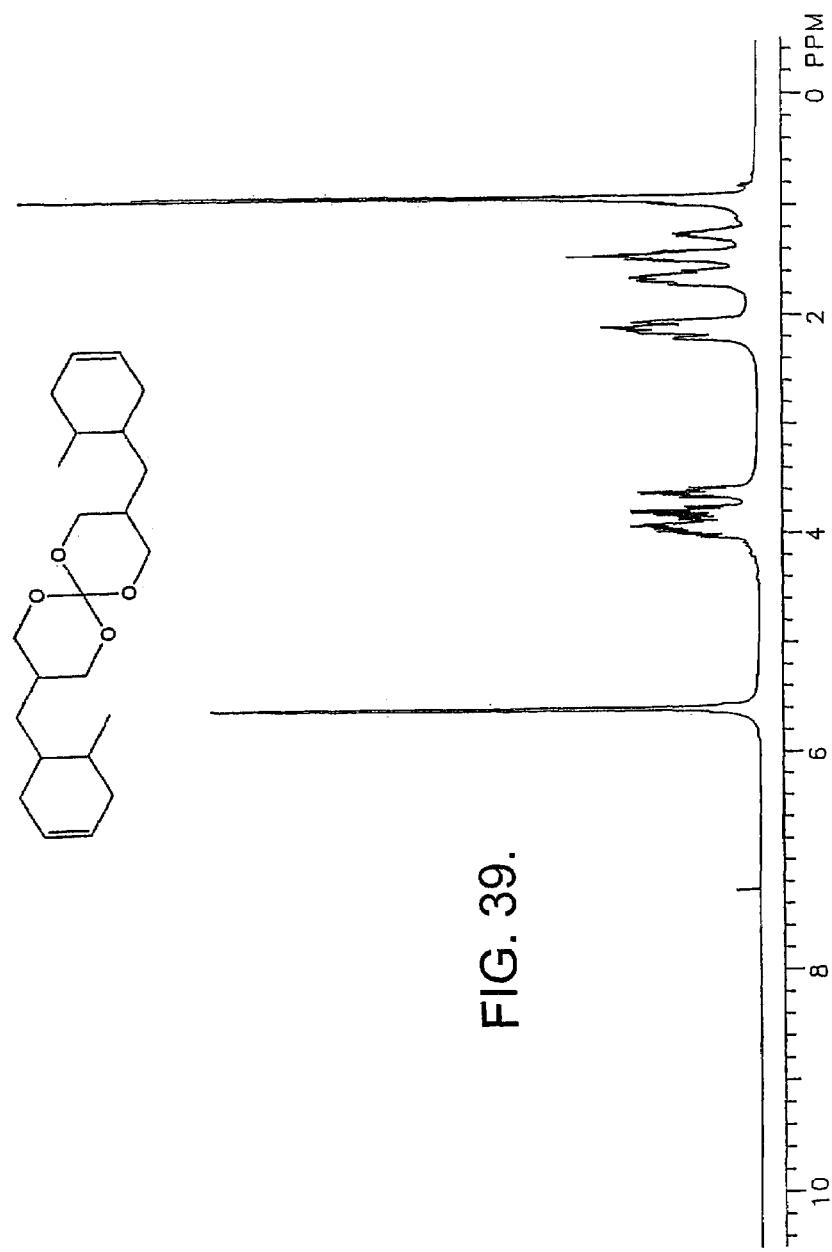
FIG. 39 is the $^1$H-NMR spectrum of 3,9-bis[(6-methylcyclohex-3-enyl)methyl]-1,5,7,11-tetraoxaspiro[5,5]undecane.
Figure 40:
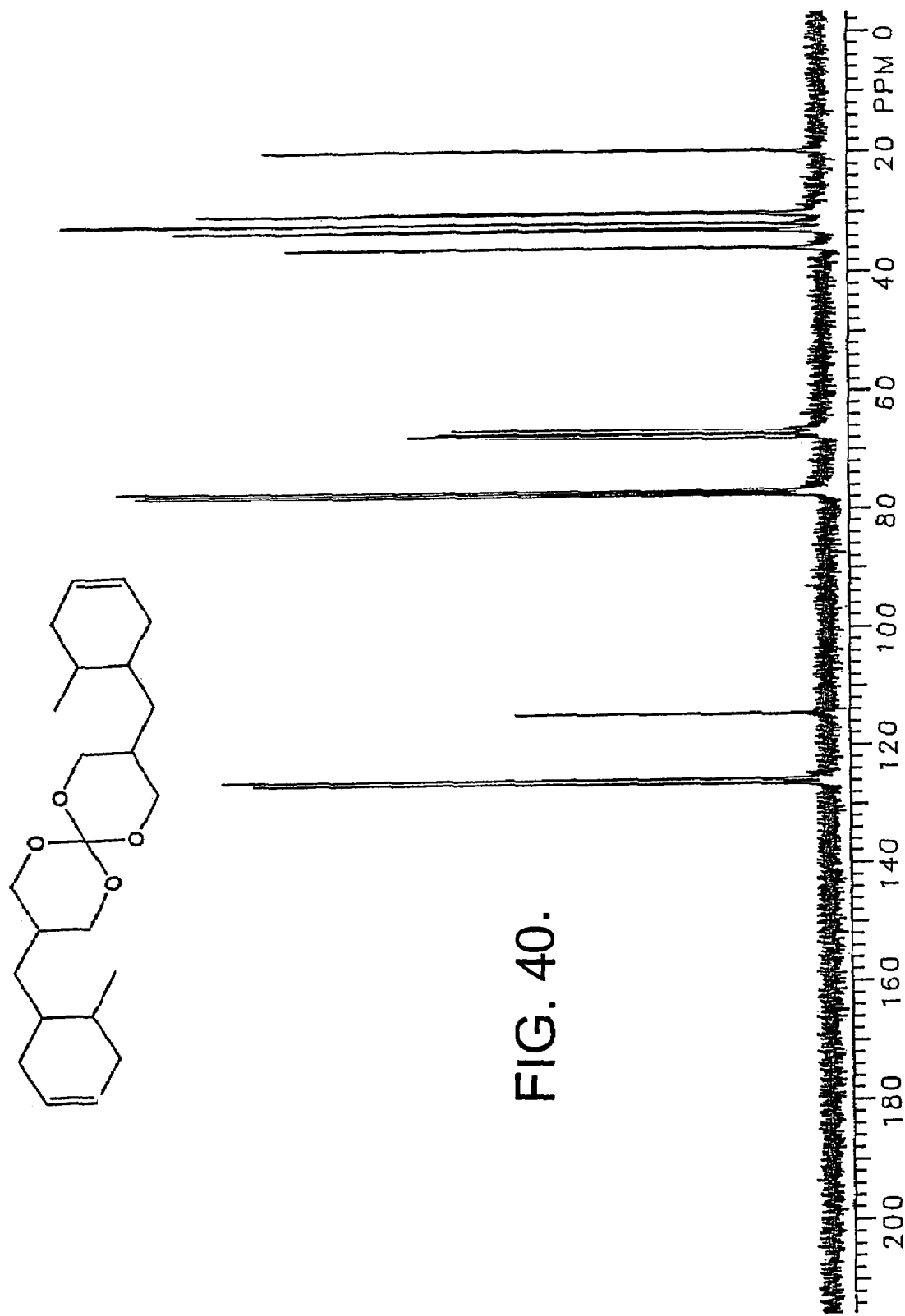
FIG. 40 is the $^1$C-NMR spectrum of 3,9-bis[(6-methylcyclohex-3-enyl)methyl]-1,5,7,11-tetraoxaspiro[5,5]undecane.
Figure 41:
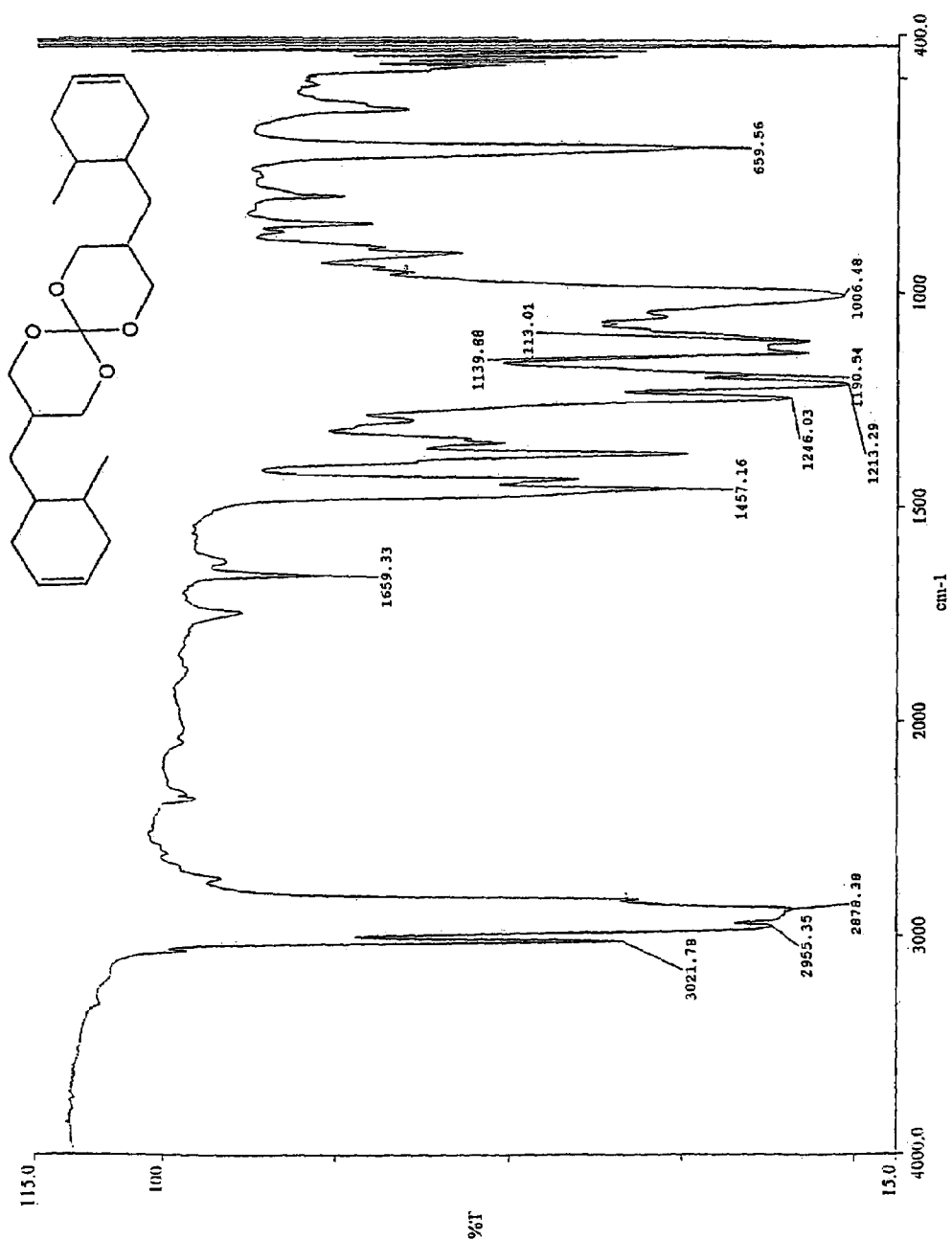
FIG. 41 is the FTIR spectrum of 3,9-bis[(6-methylcyclohex-3-enyl)methyl]-1,5,7,11-tetraoxaspiro[5,5]undecane.

A three-necked round bottomed 500 mL flask, equipped with a Dean-Stark trap (20 mL), a reflux condenser, a thermometer, a magnetic stirrer bar was charged with 1-(6-Methyl-3-cyclohexane)-2-methylene-propanediol 10.95 g (0.0594 mole) and toluene 300 mL. The mixture was brought up to reflux and kept refluxing for 2 hours to azeotropically remove any moisture. About 40 mL of azeotropic mixture was collected in the trap. Then, blanketed with $N_2$, the mixture was allowed to cool down to room temperature, and 0.2 g of anhydrous p-toluenesulfonic acid (p-TSA) was added, followed by a dropwise addition of tetraethylorthocarbonate (TEOC) 6.3 mL (prepared in-house, GC purity 99.7%, 0.03 mole). The reaction mixture was then brought up to reflux to azeotropically remove EtOH generated during the reaction. The total azeotropic mixture collected from the Dean-Stark trap (135 mL) was shaken with salt water to determine the EtOH volume. (5.5 mL). TLC (silica gel, $Et^2O$/hexanes 1/1, V/V) showed that the starting diol (Rf 0.04) had disappeared, and a new spot (Rf 0.68) was observed. The reaction mixture was now allowed to cool down to room temperature and was neutralized with 1 mL of triethylamine. The resulting mixture (pH ~8) was stirred for 30 min and was concentrated under reduced pressure. This crude oil was purified twice by flash chromatography 1 (silica gel, $Et^2O$/hexanes 1/5.6 to 1/4, V/V) and flash chromatography 2 (silica gel, $Et^2O$/hexanes 1/7 to 1/5, V/V). 3,9-Bis[1-methylene-2-(-6-methyl -3-cyclohexene)]-1,5,7,11-tetraoxaspiro[5.5]undecane was obtained in 56.8% yield as a colorless, viscous oil. $^1$H-NMR (CDCl3, 300MHz) δ 5.65-5.56 (m, 4H, 4.02-3.78 (m, 6H), 3.65-3.58 (m, 2H), 2.20-2.05 (m, 6H), 1.72-1.58 (m, 5H), 1.50-1.40 (m, 4H), 1.06-1.04 (m, 2H), 1.00-0.91 (m, 7H); $^{13}$C-NMR (CDCl3, 300MHz) §126.12, 125.41, 114.38, 67.78, 67.20, 66.88, 66.26, 35.75, 32.83, 32.71, 32.64, 31.67, 30.05, 29.87, 29.83, 19.54; FT-IR (neat, cm$^{-1}$) 3021, 2955, 2878, 1659, s1457, 1246, 1213, 1191, 1140, 1113, 1006, 660; Anal. Calcd. for $C_{23}H_{36}O_4$: C, 73.37; H, 9.64; Found: C, 73.09; H, 9.58. The $^1$H-NMR Spectrum, the ° C-NMR Spectrum, and the FTIR Spectrum of 3,9-bis-[1-methylene-2-(-6-methyl-3-cyclohexene)]-1,5,7,11-tetraoxaspiro[5,5]undecane (BMCHEM) are shown in FIGS. 39-41, respectively.

Figure 42:
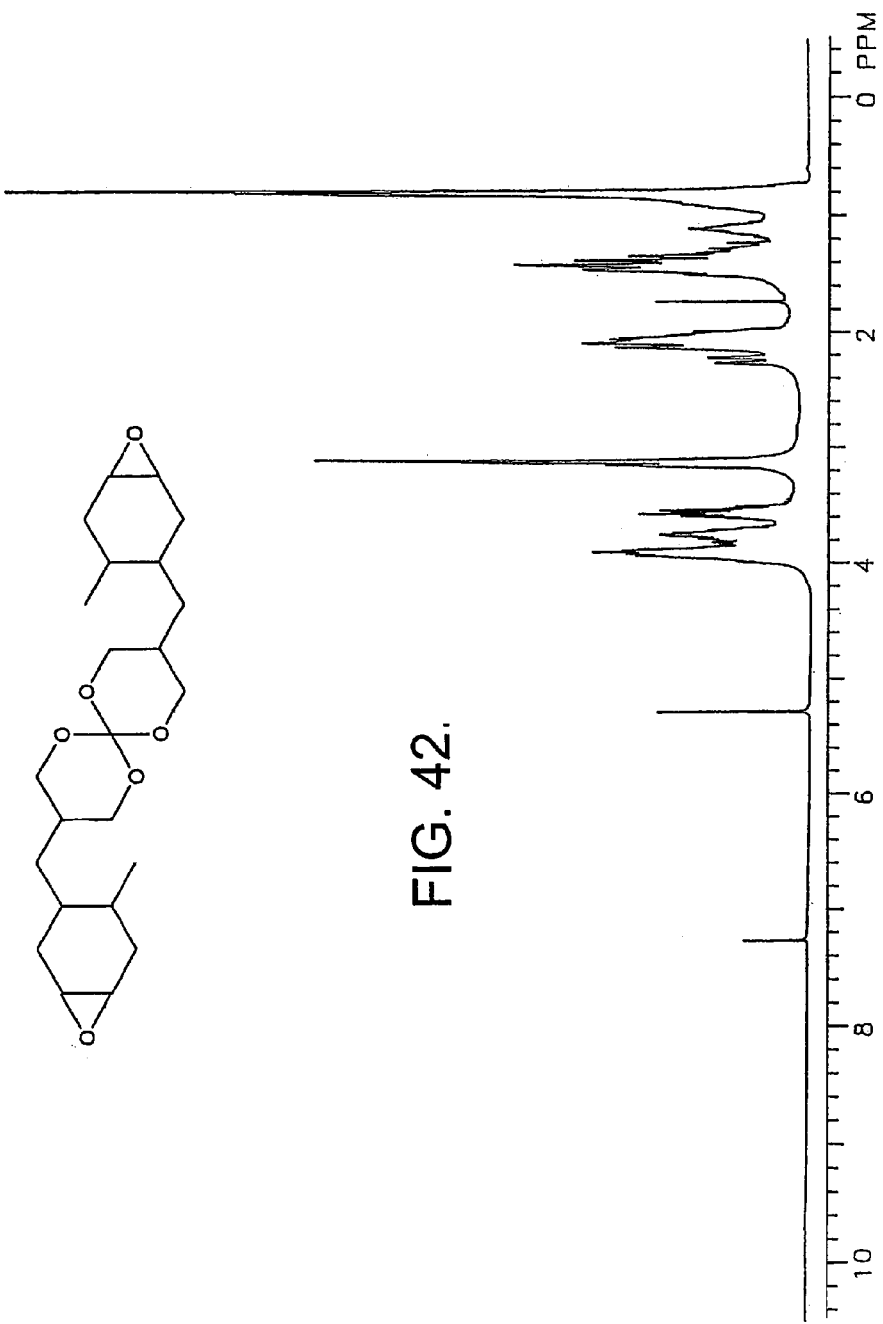
FIG. 42 is the $^1$H-NMR spectrum of 3,9-bis[(4-methyl-7-oxabicyclo[4.1.0]hept-3-yl)methyl]-1,5,7,11-tetraoxaspiro[5,5]undecane.
Figure 43:
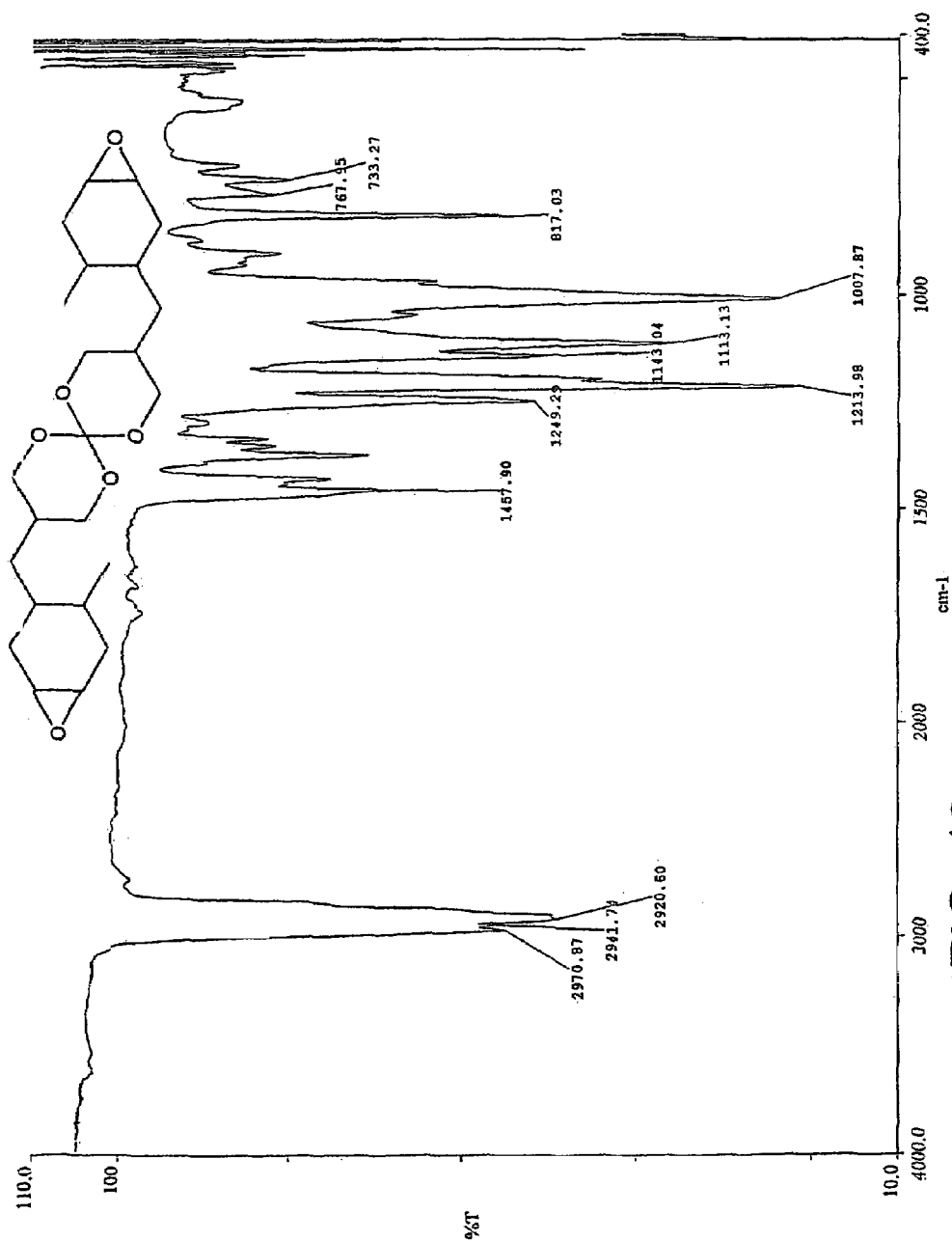
FIG. 43 is the FTIR spectrum of 3,9-bis[(4-methyl-7-oxabicyclo[4.1.0]hept-3-yl)methyl]-1,5,7,11-tetraoxaspiro[5,5]undecane.

The spiroorthocarbonate BMOCHM was prepared employing biphasic epoxidation due to the acid sensitive nature of this compound. A 1 L round bottomed flask was charged with a 3,9-bis[1-methylene-2-(-6methyl-3-cyclohexene)]-1,5,7,11-tetraoxaspiro[5,5]undecane 5.8 g (0.0154 mole) and methylene chloride ($CH_2Cl_2$) 230 mL. To this solution was added sodium bicarbonate 0.5 M aqueous solution 96 mL. The resultant mixture was allowed to stir vigorously at room temperature and then m-chloroperbenzoic acid, mCPBA (Aldrich, 77% max, 0.0316 mole) 8.6 g was added in several portions over a duration of 30 minutes. The reaction mixture was monitored by TLC (silica gel, $Et^2O$/hexanes 1/1, V/V) and thus stirred overnight. TLC showed the starting compound BMCHEM RF 0.77 had disappeared and a new spot Rf 0.17 was present. The 2 phases were then separated, and the organic phase was washed twice with 1 N aqueous NaOH 150 mL followed with water (2×150 mL) until the pH reached ~7. The aqueous phase was back extracted with $Et^2O$ and was washed with NaOH/$H_2O$ likewise until the pH reached ~7. The washed organic phases were combined, dried over anhydrous $Na_2SO_4$ and concentrated under reduced pressure to produce a crude viscous oil. This product was purified twice by flash chromatography (silica gel, 2% triethylamine, $CH_2Cl_2$/$Et^2O$ 12/1 to 4/1, V/V). After stripping the product of volatile materials and drying it extensively under reduced pressure, a colorless amorphous material of a mixture of diastereomers of 3,9-bis[(4-methyl-7-oxabicyclo[4.1.0] hept-3-yl)methyl]-1,5,7,11-tetraoxaspiro[5.5]undecane 5.6 g (89.3% yield) was procured. $^1$H-NMR (CDCl3, 300 MHz) § 3.98-3.50 (m, 8H), 3.15-3.08 (m, 4H), 2.26-1.99 (m, 6H), 1.50-1.27 (m, 8H), 1.14-1.06 (m, 2H) 0.92-0.76 (m, 8H); $^{13}$C-NMR (CDCl3, 300 MHz) § 114, 67.76, 67.69, 67.15, 66.55, 65.97, 65.92, 52.72, 52.59, 51.75, 51.46, 35.47, 35.38, 34.24, 33.17, 32.85, 32.07, 31.63, 31.58, 31.19, 31.13, 31.09, 29.86, 29.77, 29.67, 29.10, 19.26, 19.22, 19.14; FT-IR ($CH_2Cl_2$, evaporated, cm$^{-1}$) 2971, 2942, 2921, 1458, 1249, 1214, 1143, 1113, 1008, 817, 768, 701; Anal. Calcd. For $C_{23}H_{36}O_6$: C, 67.62, H, 8.88; Found C, 67.17, H, 9.09. The $^1$H-NMR Spectrum and the FTIR Spectrum of 3,9-bis[(4-methyl-7-oxabicyclo[4.1.0]hept-3-yl)methyl]-1, 5,7,11-tetraoxaspiro[5.5]undecane (6) (BOCHM-TOSU) are shown in FIGS. 42-43, respectively.

EXAMPLE 10

Figure 44:
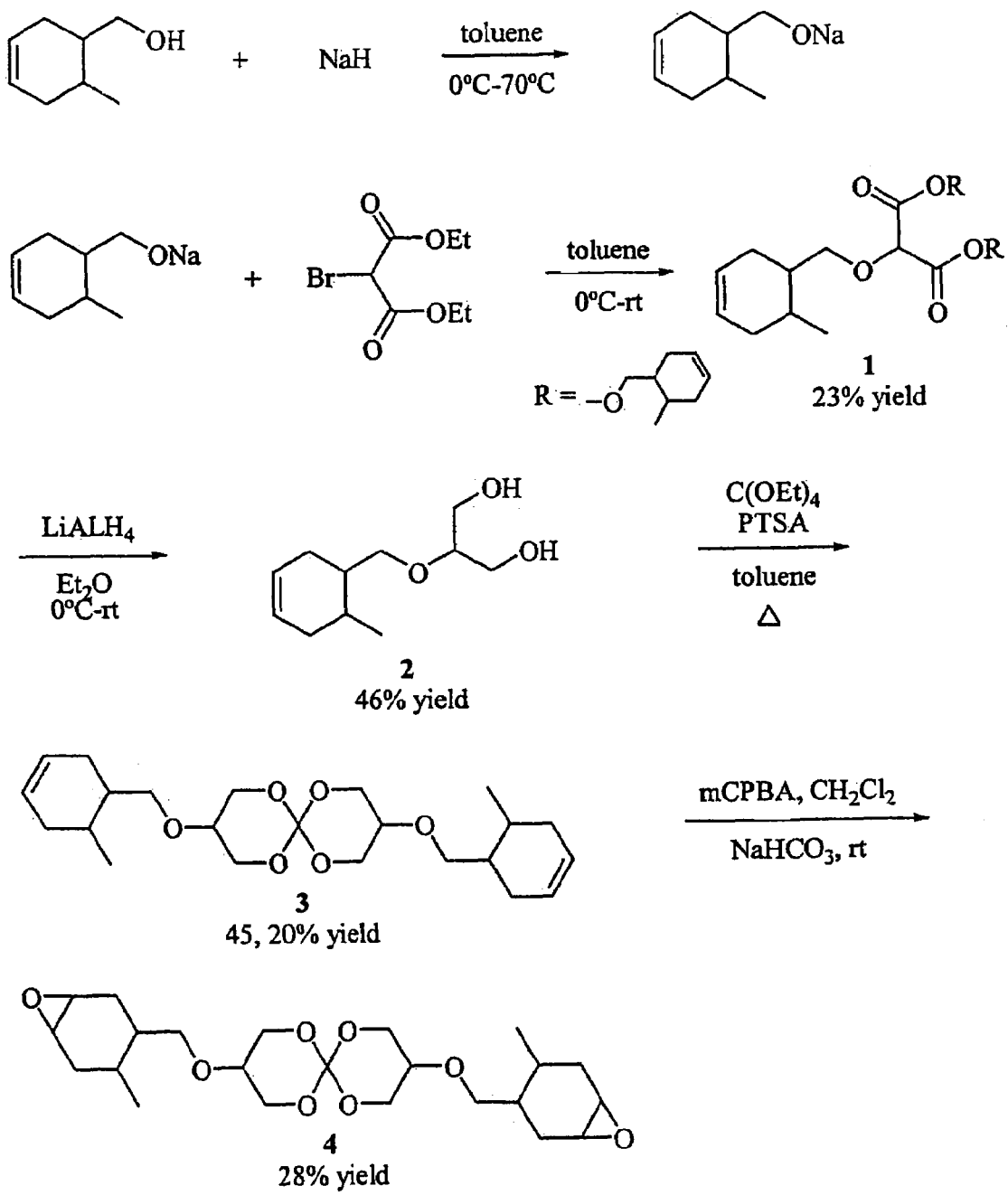
FIG. 44 is the synthesis scheme of 3,9-bis[(6-methylcyclohex-3-enyl)methoxy]-1,5,7,11-tetraoxaspiro[5,5]undecane and 3,9-bis[(4-methyl-7-oxabicyclo[4.1.0]hept-3-yl)methoxy]-1,5,7,11-tetraoxaspiro[5,5]undecane.

3,9-bis[2-methyl-7-oxabicyclo[4.1.0]hept-3-yl)methoxy]-1,5,7,11-tetraoxaspiro[5.5]undecane (BMCHEMO) and 3,9-bis[(4-methyl-7-oxabicyclo[4.1.0]hept-3-yl)methoxy]-1,5,7,11-tetraoxaspiro[5.5]undecane (BMOCHMO) were prepared. The synthetic sequence employed in the preparation of the diepoxidized cyclohexenymethoxy tetraoxaspiro[5.5]undecane is shown in FIG. 44.

To a flame-dried three-necked 1 L round-bottomed flask equipped with a magnetic stir bar, a reflux condenser, a dropping funnel, and a thermometer was placed sodium hydride (Aldrich, 60% dispersion in mineral oil, 31.68 g, 792 mmol) under an atmosphere of nitrogen. This NaH was washed with hexanes (3×150 mL) and the hexanes wash was removed via a syringe. The oil free NaH was allowed to dry by passing through a stream of nitrogen. To this oil free NaH was added toluene (500 mL), and the resulting heterogeneous mixture was allowed to cool to 0° C. To the cold suspension was then added dropwise a solution of 6-methylcyclohex-enylmethanol (Aldrich, 97%, 103.04 g, 108 mL, 792 mmol) in toluene (100 mL) through the dropping funnel over a period of 60 minutes. Bubbles evolved and white solid formed. The resulting mixture was allowed to slowly warm to room temperature and stir overnight. The reaction mixture was brought to 70° C. and stirred for 5 hours. (Note: stirring without heating yielded lower generation of the desired sodium alkoxide as shown by TLC analysis and the end result of the next coupling reaction.) The reaction mixture was allowed to cool to 0° C., and then a solution of diethyl 2-bromomalonate (Avocado, 95%, 60.40 g, 43.08 mL, 240 mmol) in toluene (50 mL) was added through the dropping funnel over a period of 30 minutes. The resulting mixture was allowed to stir at room temperature overnight. The white solid was consumed, and the reaction solution turned brown. The reaction mixture was washed with water (3×450 mL) and saturated aqueous solution of NaCl (500 mL) successfully. The aqueous phases were combined and back extracted with toluene (2×500 mL). The organic phases were combined, dried over anhydrous sodium sulfate, filtered and concentrated under reduced pressure to give reddish orange liquid. The crude material was subject to vacuum distillation and the product was collected at 170-235° C./0.75 mmHg as a mixture of the starting mono alcohol and diastereomers of possibly three diesters (di-6-methylcyclohex-3-enylmethyl-, diethyl- and ethyl 6-methylcyclohex-3-enylmethyl-). The distillate was purified by column chromatography (silica gel, 5% ethyl ether/hexanes). The desired product, di(6-methylcyclohex-3-enyl)methyl 2-[(6-methylcyclohex-3-enyl)methoxy]propane-1,3-dioate, was collected as a mixture of the three possible diesters in 15.5% yield (16.54 g). Note: Purification of the crude material by flash chromatography without prior distillation gave better results. The mixture of diesters was collected in 22.8% yield (24.3 g) along with a mixture of the diesters and the starting mono alcohol (30.15 g). $^1$H-NMR (CDCl3, 300 MHz, diastereomeric mixture of possible diesters) δ 5.58 (m, 4H), 4.44-3.94 (m, 5H), 3.64-3.33 (m, 2H), 2.24-1.56 (m, 13H), 1.31-1.14 (m, 1H), 0.99-0.83 (m, 6H); $^{13}$C-NMR (CDCl3, 300 MHz, diastereomeric mixture of possible diesters) δ 166.76, 166.58, 126.05, 125.72, 125.64, 125.57, 125.51, 125.22, 125.14, 124.94, 124.49, 124.41 79.42, 74.10, 68.12, 67.88, 66.88, 41.59, 38.40, 35.91, 32.97, 32.00, 29.50, 29.45, 29.34, 27.74, 27.68, 27.62, 25.44, 19.20, 19.10, 14.75, 13.95; FTIR (neat) (cm$^{-1}$) 3024, 2960, 2899, 2837, 1744, 1655, 1458, 1436, 1381, 1265, 1148, 1013, 662.

To a flame-dried 1 L round-bottomed flask was placed a mixture of lithium aluminum hydride powder (Aldrich, 95%, 5.88 g, 147.2 mmol) and anhydrous diethyl ether (210 mL). The mixture was allowed to stir while cooling to 0° C. To this cold LAH suspension was then added dropwise a solution of di(6-methylcyclohex-3-enyl)methyl 2-[(6-methylcyclohex-3-enyl)methoxy]propane-1,3-dioate 1 (mixture as discussed above, 20.93 g, 47.07 mmol) in anhydrous diethyl ether (30 mL) through a dropping funnel over a period of 60 minutes. The resulting mixture was allowed to stir for five (5) hours at 0° C. and then slowly warmed to room temperature. The reaction mixture was allowed to stir overnight at room temperature. The reaction mixture was then diluted with diethyl ether (250 mL), cooled to 0° C., and quenched by dropwise addition of methanol (25 mL). The resulting mixture was allowed to stir for 30 minutes and then slowly poured into an aqueous solution of saturated Rochelle salt (500 mL) at 0° C. The resulting mixture was allowed to stir while it slowly came to room temperature and the gray metal solid became white. The aqueous layer was separated and extracted with diethyl ether (2×300 mL). The combined organic phase was washed with water (2×500 mL), dried over anhydrous sodium sulfate, filtered and concentrated under reduced pressure to give a pale yellow oil which was shown to be mainly a mixture of 6-methylcyclohex-3-enylmethanol by-product and the desired diol, 2-[(6-methylcyclohex-3-enyl)methoxy]propane-1,3-diol, by TLC analysis. The crude material was purified by column chromatography (silica gel, 50% diethyl ether/hexanes). The desired 2-[(6-methylcyclohex-3-enyl)methoxy]propane-1,3-diol was obtained as colorless liquid in 46.3% yield (4.36 g) along with 7.9% yield (0.74 g) of slightly impure product and a mixture (15.53 g) of the desired diol and 6-methylcyclohex-3-enylmethanol. $^1$H-NMR (CDCl3, 300 MHz) δ 5.59 (m, 2H), 3.77-3.55 (m, 5H), 3.51-3.36 (m, 2H), 2.65 (broad s, 2H), 2.22-1.22 (m, 6H), 0.97-0.82 (m, 3H); $^{13}$C-NMR (CDCl3, 300 MHz) § 126.00, 125.66, 79.70, 72.60, 61.86, 61.78, 39.64, 32.92, 29.57, 27.95, 19.33; FTIR (neat) (cm$^{-1}$) 3367, 3023, 2957, 2887, 2833, 1655, 1435, 1378, 1073, 659.

Figure 45:
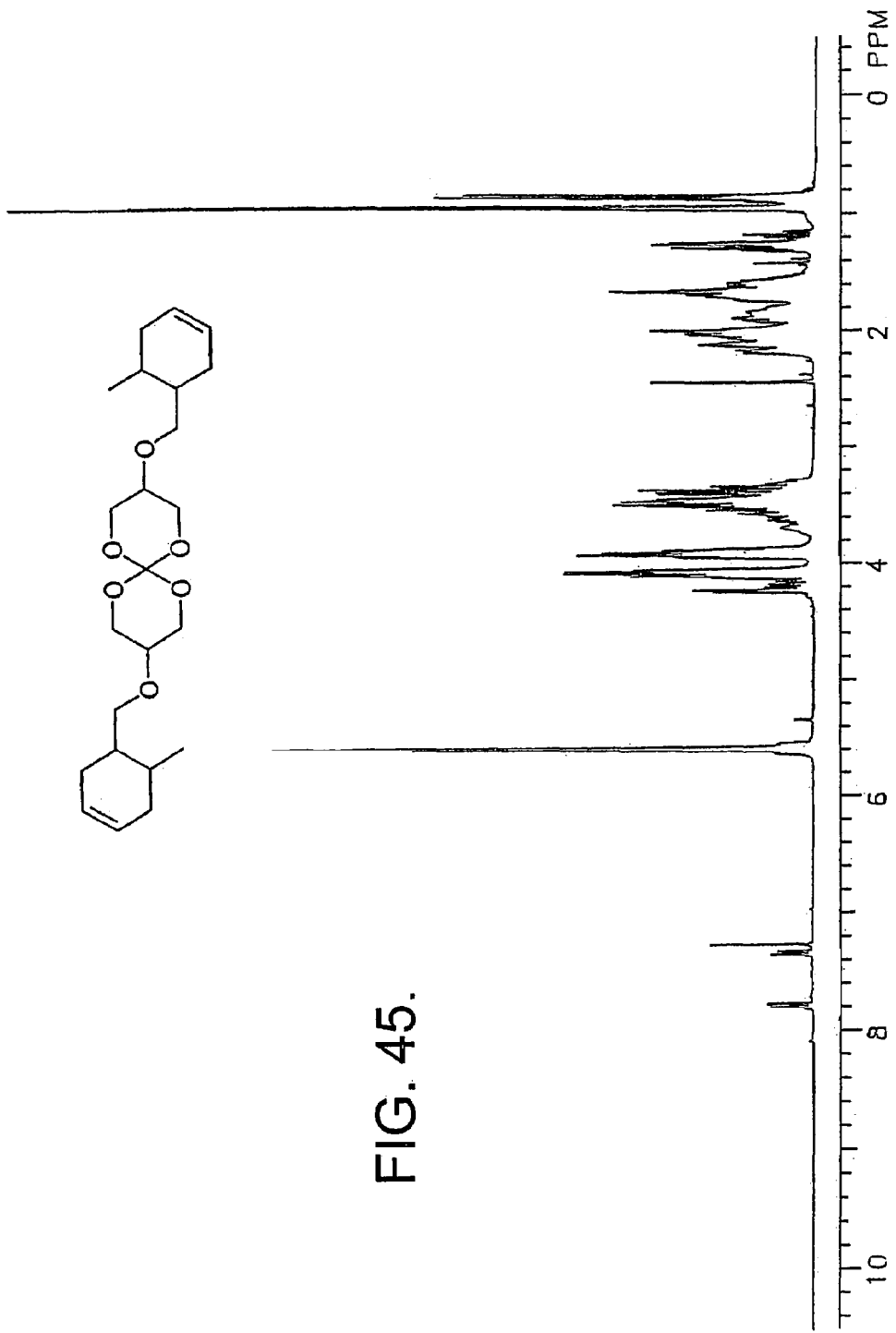
FIG. 45 is the $^1$H-NMR spectrum of 3,9-bis[(6-methylcyclohex-3-enyl)methoxy]-1,5,7,11-tetraoxaspiro[5,5]undecane.
Figure 46:
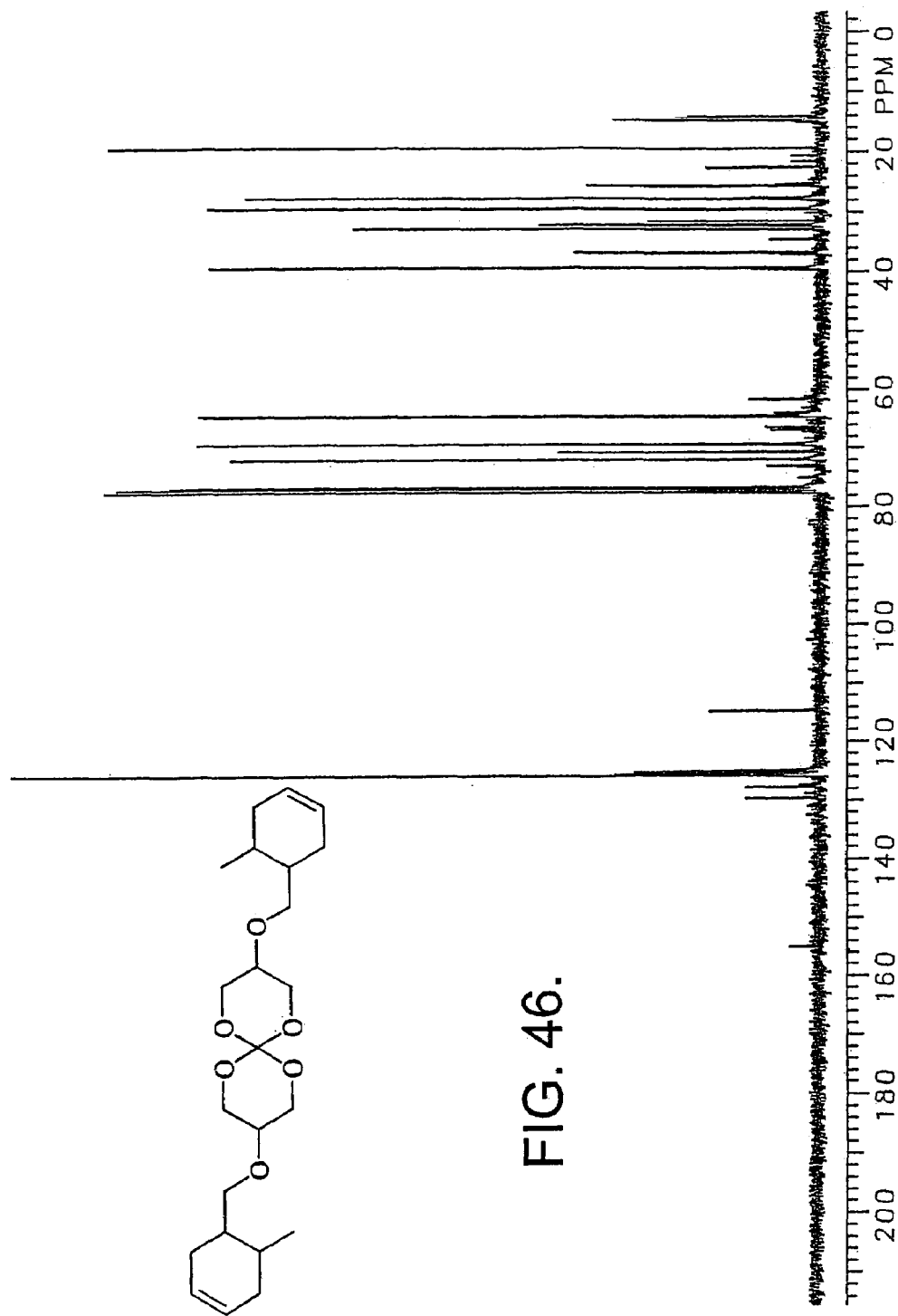
FIG. 46 is the $^1$C-NMR spectrum of 3,9-bis[(6-methylcyclohex-3-enyl)methoxy]-1,5,7,11-tetraoxaspiro[5,5]undecane.
Figure 47:
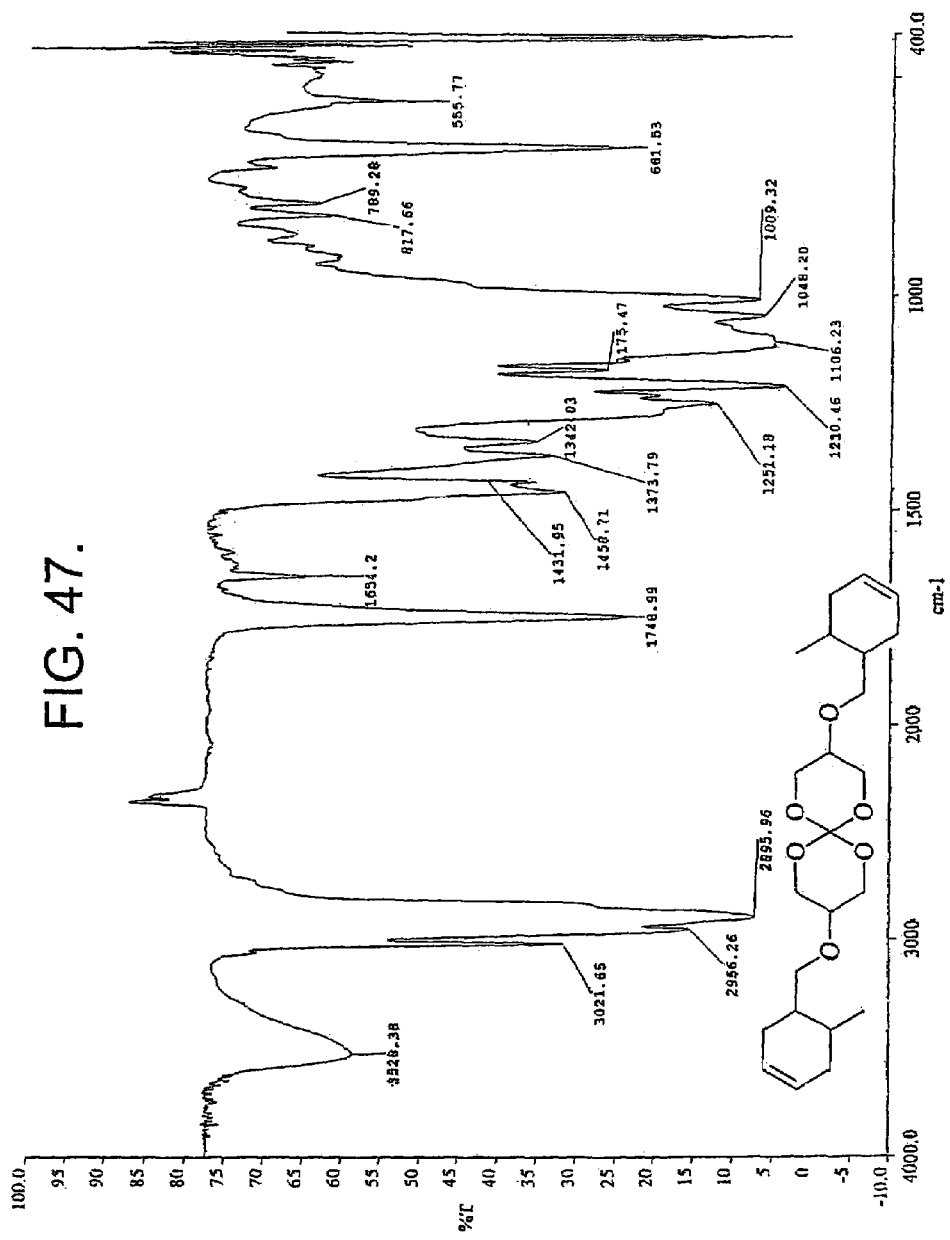
FIG. 47 is the FTIR spectrum of 3,9-bis[(6-methylcyclohex-3-enyl)methoxy]-1,5,7,11-tetraoxaspiro[5,5]undecane.

To a three-necked 250 mL flask equipped with a magnetic stir bar, a Dean-Stark trap, a reflux condenser and a thermometer was placed a mixture of toluene (150 mL) and 2-[(6-methylcyclohex-3-enyl)methoxy]propane-1,3-diol 2 (7.22 g, 36 mmol). The solution was brought to reflux to remove water azeotropically. The solution was maintained at reflux temperature for 2 hours, and 13 mL of azeotropical mixture was removed from the Dean-Stark trap. The mixture was allowed to cool to room temperature, and then anhydrous p-toluene sulphonic acid (PTSA, 0.15 g) was added followed by the addition of tetraethyl orthocarbonate (TEOC, 3.77 mL, 8.03 mmol) via a syringe. The resulting mixture was then brought to reflux to azeotropically remove, through the Dean-Stark trap, the by-product ethanol thus formed during the course of reaction. About 80 mL of the azeotropical mixture was removed, which contained 4.2 mL of ethanol (the azeotropic mixture was shaken with salty water to determine the amount of ethanol collected). The reaction mixture was allowed to stir overnight at 109° C. The reaction mixture was allowed to cool to room temperature, and then triethylamine (0.6 mL) was added to neutralize the reaction mixture. The resulting mixture was allowed to stir at room temperature for an additional 30 minutes, transferred to a 500 mL round-bottomed flask, and concentrated under reduced pressure to give light yellow oily product (6.75 g). The crude product was shown to contain mainly two spots of TOC analysis (silica gel, 10% or 50% diethyl ether/hexanes). The crude material was purified by flash chromatography (silica gel, 20-40% diethyl ether/hexanes). The product thus collected (3.28 g, 45% yield) contained some amount of the starting diol, as shown by TLC analysis. This purified material was purified a second time by column chromatography (silica gel, 25-50% ethyl ether/hexanes). The desired product, 3,9-bis[(6-methylcyclohex-3-enyl)methoxy]-1,5,7,11-tetraoxaspiro[5.5]undecane (BMCHEMO), was obtained as viscous light yellow oil in 20% yield. $^1$H-NMR (CDCl3, 300 MHz, mixture of diastereomers) § 5.57 (m, 4H), 4.25-3.25 (m, 14H), 2.20-1.22 (m, 12H), 0.98-0.80 (m, 6H); $^{13}$C-NMR (CDCl3, 300 MHz, mixture of diastereomers) δ 125.77, 125.74, 114.72, 114.68, 71.86, 69.28, 64.64, 64.37, 39.30, 32.78, 29.39, 27.70, 19.27; FTIR (neat) (cm$^{-1}$) 3022, 2956, 2896, 1654, 1459, 1432, 1374, 1342, 1251, 1210, 1175, 1106, 1048, 1009, 662. The $^1$H-NMR Spectrum, the $^1$C-NMR Spectrum, and the FTIR Spectrum of 3,9-bis-[(6-methylcyclohex-3-3nyl)methoxy]-1,5,7,11-tetraoxaspiro[5,5]undecane (BM-CHEM) are shown in FIGS. 45-47, respectively. The desired BMCHEMO-TOSU seemed to decompose on silica gel as indicated by FTIR spectral analysis which shows OH and C=O functionalities.

Figure 48:
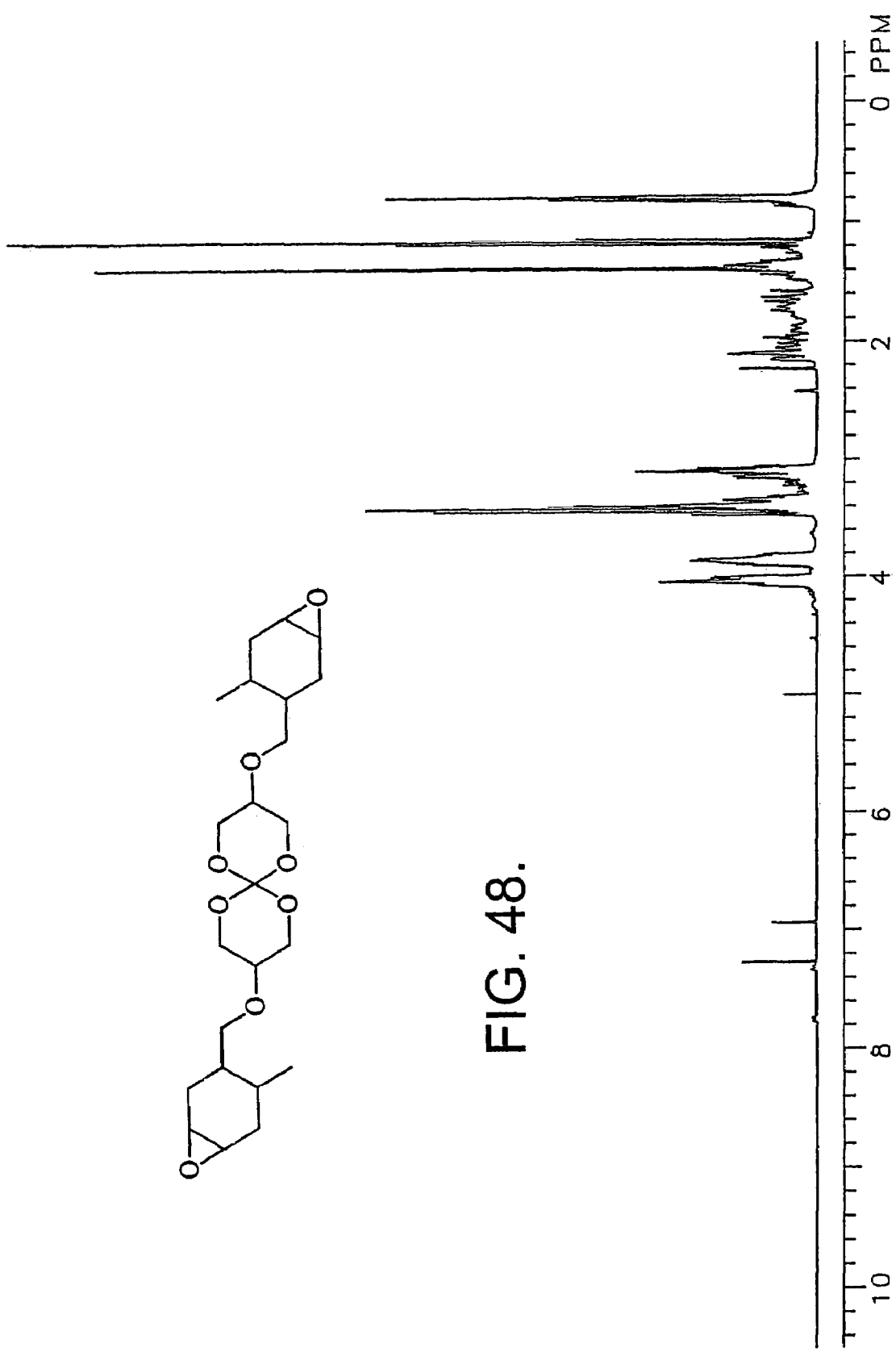
FIG. 48 is the $^1$H-NMR spectrum of 3,9-bis[(4-methyl-7-oxabicyclo[4.1.0]hept -3-yl)methoxy]-1,5,7,11-tetraoxaspiro[5,5]undecane.
Figure 49:
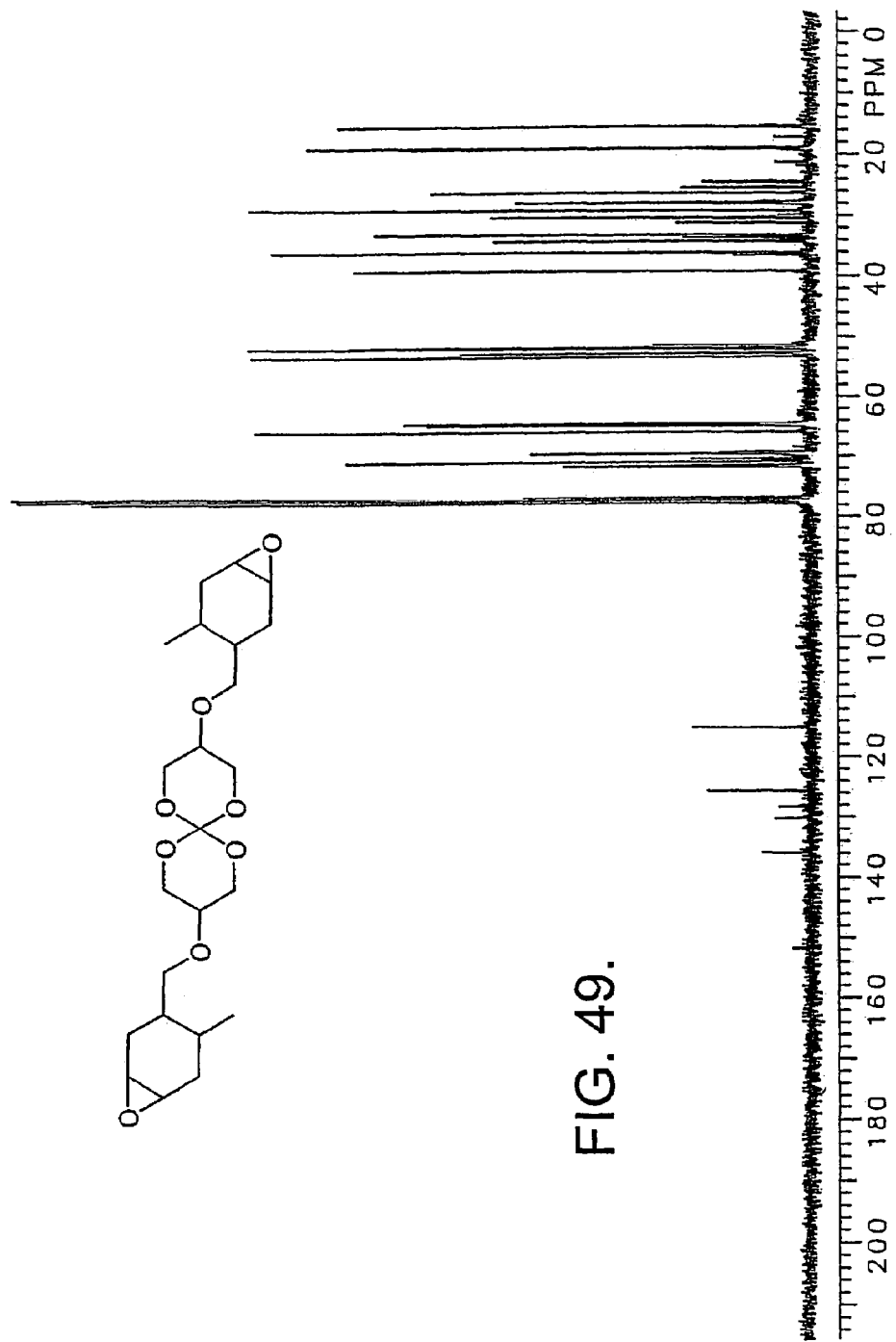
FIG. 49 is the $^1$C-NMR spectrum of 3,9-bis[(4-methyl-7-oxabicyclo[4.1.0]hept-3-yl)methoxy]-1,5,7,11-tetraoxaspiro[5,5]undecane.
Figure 50:
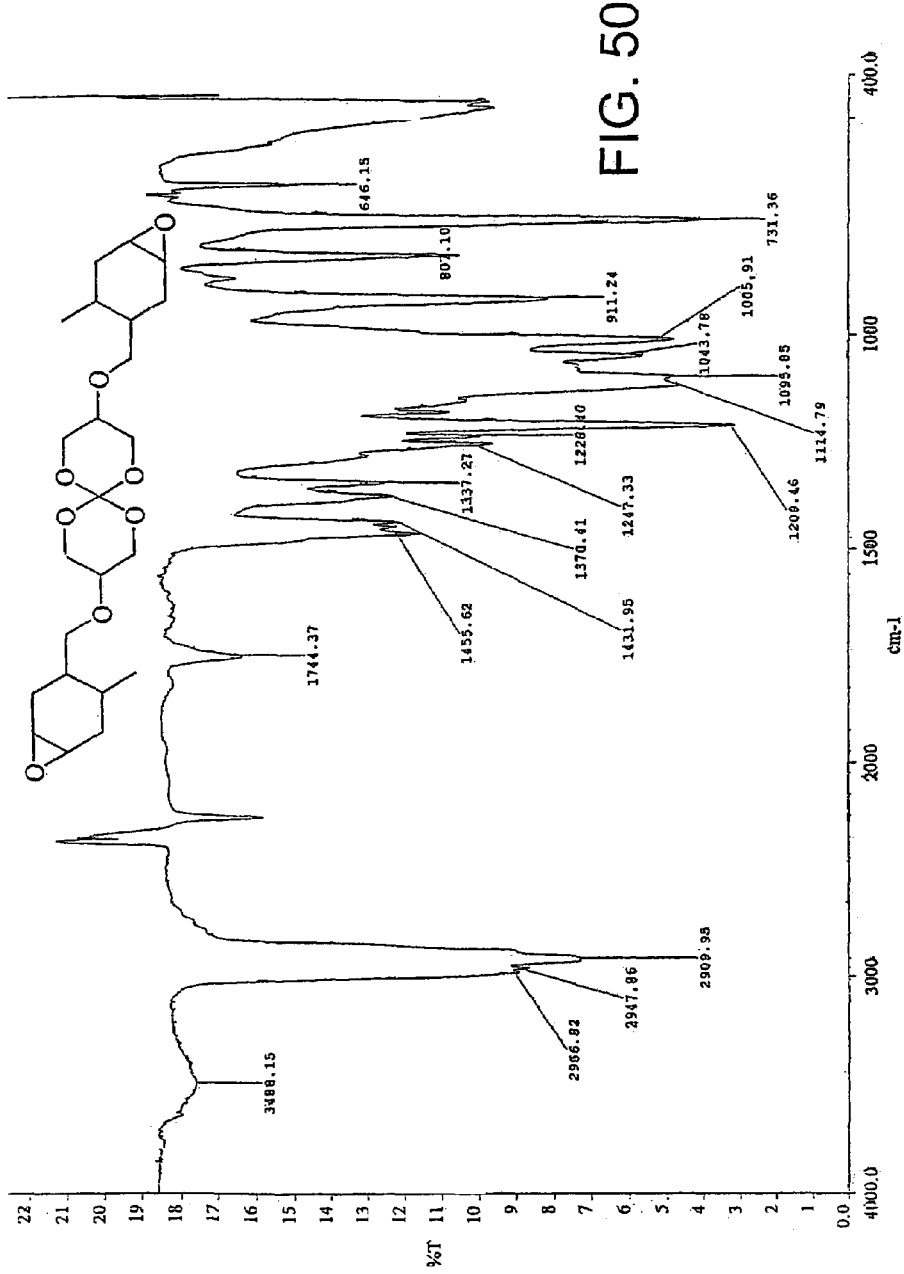
FIG. 50 is the FTIR spectrum of 3,9-bis[(4-methyl-7-oxabicyclo[4.1.0]hept-3-yl)methoxy]-1,5,7,11-tetraoxaspiro[5,5]undecane.

3,9-Bis[(4-methyl-7-oxabicyclo[4.1.0]hept-3-yl)methoxy]-1,5,7,11-tetraoxaspiro[5.5]undecane (BMOCHMO) was prepared employing biphasic epoxidation due to the acid sensitive nature of this class of compounds. To a 100 mL round-bottomed flask was placed a mixture of 3,9-bis [(6-methylcyclohex-3-enyl)methoxy]-1,5,7,11-tetraoxaspiro[5.5]undecane (impure sample containing decomposition product as indicated by FTIR spectrum which shows OH and C=O functionalities) (BMCHEMO-TOSU 3, 1.45 g, 3.55 mmol) and 50 mL of methylene chloride (CH$_2$Cl$_2$). To this solution was added 0.5 M of an aqueous solution of sodium bicarbonate (25 mL, pH ~8). The resulting biphasic mixture was allowed to stir vigorously at room temperature, and then m-chloroperbenzoic acid (Aldrich, 77% max., mCPBA, 1.75, g, ~7.81 mmol) was slowly added in several portions over a period of 30 minutes. The resulting mixture was allowed to stir for an additional 5 hours at room temperature, and the reaction progress monitored by TLC (silica gel, 50% ether/hexanes). The two phases were separated, and the organic phase was diluted with methylene chloride 930 mL) and washed successively with 1 N aqueous NaOH (2×60 mL) and water (2×50 mL). The combined aqueous phase was back extracted with methylene chloride (2×100 mL). The organic phases were combined, dried over anhydrous Na$_2$SO$_4$, filtered and concentrated under reduced pressure to give viscous yellow oil. The crude material was purified by flash chromatography (2% NEt3 deactivated silica gel, 40-60% ethyl ether/hexanes). The desired product BMOCHMO-TOSU was obtained as light yellow oil in 27.6% yield. $^1$H-NMR (CDCl3, 300 MHz, mixture of diastereomers) δ 4.08-3.98 (m, 4H), 3.90-3.80, (m, 4H), 3.48-3.04, (m, 10H), 2.16-1.20 (m, 12H), 0.87-0.76 (m, 6H), $^{13}$C-NMR (CDCl3, 300 MHz, mixture of diastereomers) δ 114.70, 114.67, 71.44, 70.67, 69.36, 69.22, 65.69, 64.53, 64.47, 64.30, 64.23, 53.06, 52.55, 51.75, 51.52, 38.95, 35.86, 33.95, 32.93, 30.15, 28.89, 28.81, 27.67, 26.10, 18.94, 18.68, 15.13; FTIR (neat) (cm$^{-1}$) 2967, 2948, 2910, 1456, 1432, 1370, 1337, 1247, 1228, 1209, 1115, 1096, 1044, 1006, 911, 807, 731. The $^1$H-NMR Spectrum, the $^1$C-NMR Spectrum, and the FTIR Spectrum of 3,9-bis[(4-methyl-7-oxabicyclo[4.1.0]hept-3-yl)methoxy]-1,5,7,11-tetraoxaspiro[5.5]undecane (BMOCHMO) are shown in FIGS. 48-50, respectively.

From the foregoing, it will be seen that this invention is one that is well adapted to attain all the ends and objects herein above set forth together with other advantages which are obvious and inherent to the composition. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. A dental matrix resin, comprising the mixture of:
   (a) a dioxiranyl 1,5,7,11-tetraoxaspiro[5.5]undecane;
   (b) a dioxirane; and
   (c) an initiator capable of initiating cationic polymerization of said resin.

2. The resin of claim 1, wherein said initiator is a photoinitiator.

3. The resin of claim 2, wherein said photoinitiator is selected from the group consisting of (4-n-octyloxyphenyl) phenyliodonium hexafluoroantimonate, [4-(2-hydroxytetradecyloxyphenyl)]phenyliodonium hexafluoroantimonate, [4-1-methylethyl)phenyl](4-methylphenyl)iodonium tetrakis(pentafluorophenyl)borate(1-), and combinations thereof.

4. The resin of claim 1, wherein said dioxiranyl tetraoxaspiro[5.5]undecane is selected from the group consisting of 3,9-bis[(7-oxabicyclo[4.1.0]hept-3-yl)-methyl]-1,5,7,11-toxaspiro[5.5]undecane, 3,9-bis[(4-methyl-7-oxabicyclo[4.1.0]hept-3-yl)methyl]-1,5,7,11-tetraoxaspiro[5.5]undecane, 3,9-Bis[(7-oxabicyclo[4.1.0]hept-3-yl)methoxy]-1,5,7,11-tetraoxaspiro[5.5]undecane, 3,9-bis[2-methyl-7-oxabicyclo[4.1.0]hept-3-yl)methoxy]-1,5,7,11-tetraoxaspiro[5.5]undecane, 3,9-bis[(4-methyl-7-oxabicyclo[4.1.0]hept-3-yl)methoxy]-1,5,7,11-tetraoxaspiro[5.5]undecane, 3,9-bis[7-oxabicyclo[4.1.0]hept-3-yl)oxymethyl]-1,5,7,11-tetraoxaspiro[5.5]undecane, 3,9-bis[(4-methyl-7-oxabiclo[4.1.0]hept-3-yl)oxymethyl]-1,5,7,11-tetraoxaspiro[5.5] undecane, 7,26-dioxatrispiro[bicycle[4.1.0]heptane-3,5'-1, 3-dioxane-2'2"-1,3-dioxane-5",4'"-bicyclo[4.1.0]heptane], and combinations thereof.

5. The resin of claim 1, wherein said dioxirane is selected from the group consisting of diglycidyl ether bisphenol A, 3',4'-epoxycyclohehanemethyl-3,4-epoxycyclohexane carboxylate, bis(2,3-oxiranylcyclopentyl)ether, butanediol diglycidyl ether, bis(3,4-epoxycyclohexylmethyl)adipate, and combinations thereof.

6. The resin of claim 1, further comprising:
   a polyol.

7. The resin of claim 6, wherein said polyol is selected from the group consisting of poly(tetrahydrofuran), 2-oxepanone polymer with 2-ethyl-2-(hydroxymethyl)-1,3-propane diol, and combinations thereof.

8. The resin of claim 1, further comprising:
   a photosensitizer.

9. The resin of claim 8, wherein said photosensitizer is selected from the group consisting of camphorquinone, 2-chlorothioxanthen-9-one, and combinations thereof.

10. The resin of claim 1, further comprising:
    a reaction promoter.

11. The resin of claim 10, wherein said reaction promoter is selected from the group consisting of ethyl p-dimethylaminobenzoate, 4,4'-bis(diethylamino)benzophenone, and combinations thereof.

12. The resin of claim 1, wherein said resin comprises about 1-30 weight % of said dioxiranyl 1,5,7,11-tetraoxaspiro[5.5]undecane, about 70-99 weight % of said dioxirane, and about 0.1-10 weight % of said initiator.

13. A dental restorative material, comprising the mixture of:
    (a) a dioxiranyl 1,5,7,11-tetraoxaspiro[5.5]undecane;
    (b) a dioxirane;

(c) an initiator capable of initiating cationic polymerization; and (d) a dental filler that does not substantially interfere with cationic polymerization.

14. A method of making a dioxiranyl 1,5,7,11-tetraoxaspiro[5.5]undecane, comprising:

providing an alkyl substituted unsaturated cyclohexenyl group bonded to a propane diol by a flexible linkage selected from the group consisting of alkylene, oxyalkylene, and alkyleneoxy linkages;

subjecting said alkyl substituted cyclo to transesterification with a tetra-alkyl -orthocarbonate to obtain an unsaturated 1,5,7,11-tetraoxaspiro[5.5]undecane; and epoxidizing said unsaturated 1,5,7,11-tetraoxaspiro[5.5]undecane with an organic per -acid to obtain a 1,5,7,11-dioxiranyl tetraoxaspiro[5.5]undecane.

15. A 1,5,7,11-tetraoxaspiro[5.5]undecane selected from the group consisting of 3,9-bis(cyclohex-3-enylmethyl)-1,5,7,11-tetraoxaspiro[5.5]undecane, 3,9-bis[(7-oxabicyclo[4.1.0]hept-3-yl)methyl]-1,5,7,11-tetraoxaspiro[5.5]undecane, 3,9-bis[(6-methylcyclohex-3-enyl)methyl]-1,5,7,11-tetraoxaspiro[5.5]undecane, 3,9-bis[(4-methyl-7-oxabicyclo[4.1.0]hept-3-yl)methyl]-1,5,7,11-tetraoxaspiro[5.5]undecane, 8,10,19,20-tetraoxatrispiro[5.2.2.5.2.2]henicosa-2,14-diene, 7,26-dioxatrispiro[bicycle[4.1.0]heptane-3,5'-1,3-dioxane-2'2"-1,3-dioxane-5",4'"-bicyclo[4.1.0]heptane], 3,9-bis(cyclohex-3-enylmethoxy)-1,5,7,11-tetraoxaspiro[5.5]undecane, 3,9-bis[(7-oxabicyclo[4.1.0]hept-3-yl)methoxy]-1,5,7,11-tetraoxaspiro[5.5]undecane, 3,9-bis[2-methyl-7-oxabicyclo[4.1.0]hept-3-yl)methoxy]-1,5,7,11-tetraoxaspiro[5.5]undecane, 3,9-bis[(4-methyl-7-oxabicyclo[4.1.0]hept-3-yl)methoxy]-1,5,7,11-tetraoxaspiro[5.5]undecane, 3,9-bis(cyclohex-3-enyloxymethyl)-1,5,7,11-tetraoxaspiro[5.5]undecane, 3,9-bis[7-oxabicyclo[4.1.0]hept-3-yl)oxymethyl]-1,5,7,11-tetraoxaspiro[5.5]undecane, 3,9-bis[(6-methylcyclohex-3-en-yl)oxymethyl]-1,5,7,11-tetraoxaspiro[5.5]undecane; and 3,9-bis[(4-methyl-7-oxabicyclo-[4.1.0]hept-3-yl)oxymethyl]-1,5,7,11-tetraoxaspiro[5,5]undecane.

16. A 1,5,7,11-tetraoxaspiro[5,5]undecane according to claim 15 which is a dioxiranyl 1,5,7,11-tetraoxaspiro[5,5]undecane selected from the group consisting of 3,9-bis[(7-oxabicyclo[4.1.0]hept-3-yl)methyl]-1,5,7,11-tetraoxaspiro[5.5]undecane, 3,9-bis [(4-methyl-7-oxabicyclo[4.1.0]hept-3-yl-)methyl]-1,5,7,11-tetraoxaspiro[5.5]undecane, 3,9-bis[(7-oxabicyclo[4.1.0]hept-3-yl)methoxy]-1,5,7,11-tetraoxaspiro[5.5]undecane, 3,9-bis[(4-methyl-7-oxabicyclo[4.1.]hept-3-y-l)methoxy]-1,5,7,11-tetraoxaspiro[5.5]undecane, 3,9-bis[7-oxabicyclo[4.1.]hept-3-yl)oxymethyl]-1,5,7,11-tetraoxaspiro[5,5]undecane, 3,9-bis[(4-methyl-7-oxabicyclo-[4.1.]hept-3-yl)oxymethyl]-1,5,7,11-tetraoxaspiro[5.5]undecane, 7,26-dioxatrispiro[bicycle[4.1.]heptane-3,5'-1,3-dioxane-2'2"-1,3-dioxane-5",4'"-bicyclo[4.1.0]heptane], and 3,9-bis[2-methyl-7-oxabicyclo[4.1.0]hept-3-yl)methoxy]-1,5,7,11-tetraoxaspiro[5.5]undecane.

17. A 1,5,7,11-tetraoxaspiro[5,5]undecane according to claim 16 which is di-substituted selected from the group consisting of 3,9-bis(cyclohex-3-enylmethyl)-1,5,7,11-tetraoxaspiro[5.5]undecane, 3,9-bis[(7-oxabicyclo[4.1.]hept-3-yl)methyl]-1,5,7,11-tetraoxaspiro[5.5]undecane, 3,9-bis[(6-methylcyclohex-3-enyl)methyl]-1,5,7,11-tetraoxaspiro[5.5]undecane, 3,9-bis[(4-methyl-7-oxabicyclo[4.1.0]hept-3-yl-)methyl]-1,5,7,11-tetraoxaspiro[5.5]undecane, 3,9-bis(cyclohex-3-enylmethoxy)-1,5,7,11-tetraoxaspiro[5.5]undecane, 3,9-bis[(7-oxabicyclo[4.1.0]hept-3-yl)methoxy]-1,5,7,11-tetraoxaspiro[5.5]undecane, 3,9-bis[(6-methylcyclohex-3-eny-1)methoxy]-1,5,7,11-tetraoxaspiro[5,5]undecane 3,9-bis[(4-methyl-7-oxabicyclo[4.1.0]hept-3-y-1)methoxy]-1,5,7,11-tetraoxaspiro[5.5]undecane, 3,9-bis(cyclohex-3-enyloxy-methyl)-1,5,7,11-tetraoxaspiro[5.5]undecane, 3,9-bis[7-oxabicyclo[4.1.0]hept-3-yl)oxymethyl]-1,5,7,11-tetraoxaspiro[5.5]undecane, 3,9-bis[(6-methylcyclohex-3-en-yl)oxymethyl]-1,5,7,11-tetraoxaspiro[5,5]undecane; and 3,9-bis[(4-methyl-7-oxabicyclo-[4.1.0]hept-3-yl)oxyrnethyl]-1,5,7,11-tetraoxaspiro[5,5]undecane, and 3,9-bis[2-methyl-7-oxabicyclo[4.1.0]hept-3-yl)methoxy]-1,5,7,11-tetraoxaspiro[5.5]undecane.

* * * * *

UNITED STATES PATENT AND TRADEMARK OFFICE
CERTIFICATE OF CORRECTION

PATENT NO. : 7,232,852 B2  
APPLICATION NO. : 10/784082  
DATED : June 19, 2007  
INVENTOR(S) : Cecil C. Chappelow et al.

Page 1 of 1

It is certified that error appears in the above-identified patent and that said Letters Patent is hereby corrected as shown below:

Column 25,  
Line 29, insert -- 3,9-bis[(6-methylcyclohex-3-eny-l)methoxy]-1,5,7,11-tetraoxaspiro[5.5]undecane -- after "oxy]-1,5,7,11-tetraoxaspiro[5.5]undecane,".

Column 26,  
Line 7, delete "[4.1.]hept-3-y-l)methoxy]-1,5,7,11-tetraoxaspiro[5.5]" and insert -- [4.1.0] hept-3-y-l)methoxy]-1,5,7,11-tetraoxaspiro[5.5] -- therefor.

Column 26,  
Line 8, delete "[4.1.]hept-3-yl)oxymethyl]-" and insert -- [4.1.0]hept-3-yl)oxymethyl]- -- therefor.

Column 26,  
Line 10, delete "[4.1.]hept-3-yl)oxymethyl]-1,5,7,11-" and insert -- [4.1.0]hept-3-yl)oxymethyl]-1,5,7,11 -- therefor.

Column 26,  
Line 11, delete "7,26-dioxatrispiro[bicycle[4.1.]" and insert -- 7,26-dioxatrispiro[bicycle[4.1.0] -- therefor.

Column 26,  
Line 19, delete "3,9-bis[(7-oxabicyclo[4.1.]hept-" and insert -- 3,9-bis[(7-oxabicyclo[4.1.0]hept- -- therefor.

Signed and Sealed this

Twenty-fifth Day of December, 2007

JON W. DUDAS  
*Director of the United States Patent and Trademark Office*